United States Patent [19]
Anderson et al.

[11] Patent Number: 5,844,090
[45] Date of Patent: Dec. 1, 1998

[54] MODIFIED HEMOGLOBIN-LIKE COMPOUNDS

[75] Inventors: David C. Anderson, San Bruno, Calif.;
Antony J. Mathews, Louisville, Colo.;
Stephen P. Trimble, Boulder, Colo.;
Spencer Anthony-Cahill, Boulder, Colo.

[73] Assignee: Somatogen, Inc., Boulder, Colo.

[21] Appl. No.: 487,431

[22] Filed: Jun. 7, 1995

Related U.S. Application Data

[63] Continuation-in-part of Ser. No. 240,712, May 9, 1994, Pat. No. 5,599,907.
[51] Int. Cl.$^6$ .................. C07K 14/805; A61K 35/14; C12P 21/02
[52] U.S. Cl. .................. 530/385; 530/829; 435/69.1; 435/69.6; 435/69.7; 435/71.1
[58] Field of Search .................. 530/385, 829; 514/6, 832; 536/23.4, 23.5; 435/69.1, 69.6, 69.7, 71.1

[56] References Cited

U.S. PATENT DOCUMENTS

| 4,001,200 | 1/1977 | Bonsen et al. | 530/385 |
|---|---|---|---|
| 4,001,401 | 1/1977 | Bonsen et al. | 514/6 |
| 4,053,590 | 10/1977 | Bonsen et al. | 514/6 |
| 4,336,248 | 6/1982 | Bonhard | 530/354 |
| 4,529,719 | 7/1985 | Tye | 514/6 |
| 4,584,130 | 4/1986 | Bucci et al. | 530/385 |
| 4,598,064 | 7/1986 | Walder | 514/6 |
| 4,600,531 | 7/1986 | Walder | 530/385 |
| 4,769,326 | 9/1988 | Rutter | 435/68.1 |
| 4,777,244 | 10/1988 | Bonhard et al. | 530/385 |
| 5,028,588 | 7/1991 | Hoffman et al. | 514/6 |
| 5,599,907 | 2/1997 | Anderson et al. | 530/385 |

FOREIGN PATENT DOCUMENTS

| 0290252 | 11/1988 | European Pat. Off. . |
|---|---|---|
| 0402300 | 12/1990 | European Pat. Off. . |
| 8809179 | 12/1988 | WIPO . |
| 9013645 | 11/1990 | WIPO . |
| 9116349 | 10/1991 | WIPO . |
| 9211283 | 7/1992 | WIPO . |
| 9309143 | 5/1993 | WIPO . |
| 9514038 | 5/1995 | WIPO . |

OTHER PUBLICATIONS

Petrella et al. "Effect of Different Heterobifunctional Crosslinks . . . " J Cell Biochem Suppl. O 10ptB 97, 1986.
Adams, J.G. et al./HB Mississippi [β44(CD3) SER–>ARG]: A New Variant with Anomalous Properties/Hemoglobin/(1987) 11(5): 435–452.
Bonaventura, J. & Riggs, A./Polymerization of Hemoglobins of Mouse and Man: Structural Basis/Science/(1967) 149: 800–802.
Chatterjee, R. et al./Isolation and Characterization of a New Hemoglobin Derivative Cross–Linked Between the α Chains (Lysine 99β$_1$—>Lysine 99βa$_2$)/J. of Biological Chem./(1986) 261: 9929–9937.
Greer, J. & Perutz, M.F./Three Dimensional Structure of Haemoglobin Rainier/Nature New Biology/(1971) 230: 261–264.
Ishimoto, G. et al./ A Variant Hemoglobin Found in Macaca Fuscata: Another Polymerizing Hemoglobin of Macaques/J. Anthrop. Soc. Nippon/(1975) 83(3): 233–243.
Kavanaugh, M.P. et al/Affinity Labeling of Hemoglobin with 4,4'–Diisothiocy Anostilbene–2,2'–Disulfonate: Covalent Cross–Linking in the 2,3–Diphosphoglycerate Binding Site/Biochemistry/(1988) 27: 1804–1808.
Riggs, A./Hemoglobin Polymerization in Mice/Science/ (1965) 147: 621–623.
Looker, D.L. et al./A Human Recombinant Haemoglobin Designed for Use as a Blood Substitute/Nature/(1992) 356: 258–260.
Snyder, S. et al./HbXL99α:A Hemoglobin Derivative That is Cross–Linked Between the α Subunits is Useful as a Blood Substitute/PNAS (USA) (1987) 84: 7280–7284.
Takenaka, O. et al./Hemoglobin Izu(Macaca): β83 (EF 7) GLY→CYS. A New Hemoglobin Variant Found in the Japanese Monkey (Macaca Fuscata)/Biochimica et Biophysica Acta/(1977) 492: 433–444.
Tam, L–T. et al./The Hemoglobins of the Bullfrog Rana Catesbeiana/J. of Biological Chem./(1986) 261(18): 8290–8294.
Tondo, C. et al/Functional Properties of Hemoglobin Pôrto Alegre ($\alpha_2^A \beta_2^{9\ SER>CYS}$) and the Reactivity of its Extra Cysteinyl Residue/(Biochimica et Biophysica Acta/(1974) 342: 15–20.
Tondo, C./Osmometric Study of the Subunit Dissociation of Hemoglobin Porto Alegre [β9(A6)SER>CYS] Dissulfide Polymer/An Acad. Bras. Ci./(1987) 59(3):243–251.
Tondo, C. et al/Kinetic Study of Hemoglobin Porto Alegre [β9(A6)SER>CYS] Disulfide Polymer Reduction/An Acad Bras. Ci./(1985) 57(4) 498–506.
Tondo, C.V./Hemoglobin Porto Alegre: An Assymetric Tetramer with Only One Abnormal Beta Chain in the Aged Hemolysate of Erythrocytes from the Heterozygous Carrier ($\alpha_2^A \beta_2^{9\ SER>CYS}$)/An Acad. Brasil. Ci./(1972) 44(2):337–348.
Honig, G.R. et al/ Hemoglobin Nigeria (α–81 SER>CYS): A New Variant Associated with α–Thalassemia/Blood/ (1980) 55(1): 131–137.
Manning et al/Evolution of a Polymeric Globin in the Brine Shrimp Artemia/Nature/(1990) 348: 653–656.
Piccinini, M. et al/Primary Structure and Oxygen–Binding Properties of the Hemoglobin from the Lesser Hedgehog Tenrec (*Echinops Telfairi*, Zalambdodonta)Biol. Chem./ (1991) 372: 975–989.

*Primary Examiner*—Nancy Degen
*Attorney, Agent, or Firm*—Theresa A. Brown

[57] ABSTRACT

The present invention relates to modified hemoglobin-like compounds. The novel compounds include a globin-like polypeptide containing at least two di-alpha domains and multimeric hemoglobin-like proteins having a core hemoglobin-like moiety directly attached to at least two other hemoglobin-like moieties. The invention also relates to nucleic acid molecules encoding the novel polypeptides. Methods of making the multimeric hemoglobin-like proteins are also provided, as well as compositions containing the proteins.

23 Claims, 2 Drawing Sheets

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 7
        ( B ) TYPE: amino acid
        ( D ) TOPOLOGY: unknown to applicant ( i i ) MOLECULE TYPE: peptide ( i i i ) HYPOTHETICAL: no ( x i ) SEQUENCE DESCRIPTION: SEQ ID NO:1:

Ser  Gly  Gly  Ser  Gly  Gly  Ser
                 5

( 2 ) INFORMATION FOR SEQ ID NO:2:

( i ) SEQUENCE CHARACTERISTICS:
    ( A ) LENGTH: 14
    ( B ) TYPE: amino acid
    ( D ) TOPOLOGY: unknown to applicant ( i i ) MOLECULE TYPE: peptide ( i i i ) HYPOTHETICAL: no ( x i ) SEQUENCE DESCRIPTION: SEQ ID NO:2:

Gly Gly Ser Gly Gly Ser Gly Gly Ser Gly Gly Ser Gly Gly
                5                      10                     15

( 2 ) INFORMATION FOR SEQ ID NO:3:

( i ) SEQUENCE CHARACTERISTICS:
    ( A ) LENGTH: 16
    ( B ) TYPE: amino acid
    ( D ) TOPOLOGY: unknown to applicant ( i i ) MOLECULE TYPE: peptide ( i i i ) HYPOTHETICAL: no ( x i ) SEQUENCE DESCRIPTION: SEQ ID NO:3:

Ser Gly Gly Ser Gly Gly Ser Gly Gly Ser Gly Gly Ser Gly Gly
                5                      10                     15

Ser ( 2 ) INFORMATION FOR SEQ ID NO:4:

( i ) SEQUENCE CHARACTERISTICS:
    ( A ) LENGTH: 45
    ( B ) TYPE: nucleic acid
    ( C ) STRANDEDNESS: single
    ( D ) TOPOLOGY: linear ( i i ) MOLECULE TYPE: C-term of a gene, Xba I site ( i i i ) HYPOTHETICAL: no ( x i ) SEQUENCE DESCRIPTION: SEQ ID NO:4:

CGGGAATACG GTCTAGATCA TTAACGGTAT TTCGAAGTCA GAACG          45

( 2 ) INFORMATION FOR SEQ ID NO:5:

( i ) SEQUENCE CHARACTERISTICS:
    ( A ) LENGTH: 95
    ( B ) TYPE: nucleic acid
    ( C ) STRANDEDNESS: single
    ( D ) TOPOLOGY: linear ( i i ) MOLECULE TYPE: tac promoter sequence, Bam HI-Eag I sites ( i i i ) HYPOTHETICAL: no ( x i ) SEQUENCE DESCRIPTION: SEQ ID NO:5:

GATCCGAGCT GTTGACAATT AATCATCGGC TCGTATAATG TGTGGAATTG          50

TGACGGATAA CAATTTCACA CAGGAAATTA ATTAATGCTG TCTCC               95

( 2 ) INFORMATION FOR SEQ ID NO:6:

( i ) SEQUENCE CHARACTERISTICS:
    ( A ) LENGTH: 96
    ( B ) TYPE: nucleic acid
    ( C ) STRANDEDNESS: single
    ( D ) TOPOLOGY: linear (i i) MOLECULE TYPE: tac promoter, Bam HI - Eag I sites (i i i) HYPOTHETICAL: no (x i) SEQUENCE DESCRIPTION: SEQ ID NO:6:

GGCCGGAGAC AGCATTAATT AATTTCCTGT GTGAAATTGT TATCCGCTCA 50

CAATTCCACA CATTATACGA GCCGATGATT AATTGTCAAC AGCTCG 96

(2) INFORMATION FOR SEQ ID NO:7:

(i) SEQUENCE CHARACTERISTICS:
 (A) LENGTH: 64
 (B) TYPE: nucleic acid
 (C) STRANDEDNESS: single
 (D) TOPOLOGY: linear (i i) MOLECULE TYPE: 5'end of alpha gene, with EcoR1, BamH1 and
 Eag1 sites (i i i) HYPOTHETICAL: no (x i) SEQUENCE DESCRIPTION: SEQ ID NO:7:

TCGGATTCGA ATTCCAAGCT GTTGGATCCT TAGATTGAAC TGTCTCCGGC 50

CGATAAAACC ACCG 64

(2) INFORMATION FOR SEQ ID NO:8:

(i) SEQUENCE CHARACTERISTICS:
 (A) LENGTH: 55
 (B) TYPE: nucleic acid
 (C) STRANDEDNESS: single
 (D) TOPOLOGY: linear (i i) MOLECULE TYPE: 5'end of beta with Xba I site (i i i) HYPOTHETICAL: no (x i) SEQUENCE DESCRIPTION: SEQ ID NO:8:

CGGAAGCCCA ATCTAGAGGA AATAATATAT GCACCTGACT CCGGAAGAAA 50

AATCC 55

(2) INFORMATION FOR SEQ ID NO:9:

(i) SEQUENCE CHARACTERISTICS:
 (A) LENGTH: 44
 (B) TYPE: nucleic acid
 (C) STRANDEDNESS: single
 (D) TOPOLOGY: linear (i i) MOLECULE TYPE: 3'end of the beta gene with Hind III site (i i i) HYPOTHETICAL: no (x i) SEQUENCE DESCRIPTION: SEQ ID NO:9:

CCCGAAACCA AGCTTCATTA GTGAGCTAGC GCGTTAGCAA CACC 44

(2) INFORMATION FOR SEQ ID NO:10:

(i) SEQUENCE CHARACTERISTICS:
 (A) LENGTH: 37
 (B) TYPE: nucleic acid
 (C) STRANDEDNESS: single
 (D) TOPOLOGY: linear (i i) MOLECULE TYPE: mutagenesis reverse primer (i i i) HYPOTHETICAL: no ( x i ) SEQUENCE DESCRIPTION: SEQ ID NO:10:

TTTAAGCTTC ATTAGTGGTA TTTGTGAGCT AGCGCGT    37

( 2 ) INFORMATION FOR SEQ ID NO:11:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i i ) MOLECULE TYPE: mutagenesis reverse primer ( i i i ) HYPOTHETICAL: no ( x i ) SEQUENCE DESCRIPTION: SEQ ID NO:11:

CAGCATTAAT TAACCTCCTT AGTGAAATTG TTATCCG    37

( 2 ) INFORMATION FOR SEQ ID NO:12:

( i ) SEQUENCE CHARACTERISTICS:
        ( A ) LENGTH: 45
        ( B ) TYPE: nucleic acid
        ( C ) STRANDEDNESS: single
        ( D ) TOPOLOGY: linear ( i i ) MOLECULE TYPE: mutagenesis reverse primer ( i i i ) HYPOTHETICAL: no ( x i ) SEQUENCE DESCRIPTION: SEQ ID NO:12:

GGTGCATATA TTTACCTCCT TATCTAGATC ATTAACGGTA TTTCG    45

( 2 ) INFORMATION FOR SEQ ID NO:13:

( i ) SEQUENCE CHARACTERISTICS:
        ( A ) LENGTH: 10
        ( B ) TYPE: nucleic acid
        ( C ) STRANDEDNESS: single
        ( D ) TOPOLOGY: linear ( i i ) MOLECULE TYPE: Pme I linker ( i i i ) HYPOTHETICAL: no ( x i ) SEQUENCE DESCRIPTION: SEQ ID NO:13:

GGTTTAAACC    10

( 2 ) INFORMATION FOR SEQ ID NO:14:

( i ) SEQUENCE CHARACTERISTICS:
        ( A ) LENGTH: 58
        ( B ) TYPE: nucleic acid
        ( C ) STRANDEDNESS: single
        ( D ) TOPOLOGY: linear ( i i ) MOLECULE TYPE: oligonucleotide upstream of lacI gene ( i i i ) HYPOTHETICAL: no ( x i ) SEQUENCE DESCRIPTION: SEQ ID NO:14:

GGCGAATAAA AGCTTGCGGC CGCGTTGACA CCATCGAATG GCGCAAAACC    50

TTTCGCGG    58

( 2 ) INFORMATION FOR SEQ ID NO:15:

( i ) SEQUENCE CHARACTERISTICS:
        ( A ) LENGTH: 69
        ( B ) TYPE: nucleic acid (C) STRANDEDNESS: single
(D) TOPOLOGY: linear (ii) MOLECULE TYPE: downstream side of lacI gene (iii) HYPOTHETICAL: no (xi) SEQUENCE DESCRIPTION: SEQ ID NO:15:

GGGCAAATAG GATCCAAAAA AAAGCCCGCT CATTAGGCGG GCTTTATCAC    50

TGCCCGCTTT CCAGTCGGG    69

(2) INFORMATION FOR SEQ ID NO:16:

(i) SEQUENCE CHARACTERISTICS:
(A) LENGTH: 54
(B) TYPE: nucleic acid
(C) STRANDEDNESS: single
(D) TOPOLOGY: linear (ii) MOLECULE TYPE: primer for pBR322 ori positions 3170-3148

(iii) HYPOTHETICAL: no (xi) SEQUENCE DESCRIPTION: SEQ ID NO:16:

CCCCGAAAAG GATCCAAGTA GCCGGCGGCC GCGTTCCACT GAGCGTCAGA    50

CCCC    54

(2) INFORMATION FOR SEQ ID NO:17:

(i) SEQUENCE CHARACTERISTICS:
(A) LENGTH: 42
(B) TYPE: nucleic acid
(C) STRANDEDNESS: single
(D) TOPOLOGY: linear (ii) MOLECULE TYPE: primer for pBR322 ori positions 2380-2404

(iii) HYPOTHETICAL: no (xi) SEQUENCE DESCRIPTION: SEQ ID NO:17:

GGCGGTCCTG TTTAAACGCT GCGCTCGGTC GTTCGGCTGC GG    42

(2) INFORMATION FOR SEQ ID NO:18:

(i) SEQUENCE CHARACTERISTICS:
(A) LENGTH: 28
(B) TYPE: nucleic acid
(C) STRANDEDNESS: single
(D) TOPOLOGY: unknown to applicant (ii) MOLECULE TYPE: Other nucleic acid (iii) HYPOTHETICAL: no (xi) SEQUENCE DESCRIPTION: SEQ ID NO:18:

CAATTTCACA GGAAATTAAT TAATGCTG    28

(2) INFORMATION FOR SEQ ID NO:19:

(i) SEQUENCE CHARACTERISTICS:
(A) LENGTH: 30
(B) TYPE: nucleic acid
(C) STRANDEDNESS: single
(D) TOPOLOGY: unknown to applicant (ii) MOLECULE TYPE: Other nucleic acid (iii) HYPOTHETICAL: no (xi) SEQUENCE DESCRIPTION: SEQ ID NO:19:

```
CAATTTCACT AAGGAGGTTA ATTAATGCTG                                              30
```

( 2 ) INFORMATION FOR SEQ ID NO:20:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: unknown to applicant ( i i ) MOLECULE TYPE: Other nucleic acid ( i i i ) HYPOTHETICAL: no ( x i ) SEQUENCE DESCRIPTION: SEQ ID NO:20:

```
TAAAGATCTA GAGGAAATAA TATATGCAC                                                29
```

( 2 ) INFORMATION FOR SEQ ID NO:21:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: unknown to applicant ( i i ) MOLECULE TYPE: Other nucleic acid ( i i i ) HYPOTHETICAL: no ( x i ) SEQUENCE DESCRIPTION: SEQ ID NO:21:

```
TAATGATCTA GATAAGGAGG TAAATATATG CAC                                          33
```

( 2 ) INFORMATION FOR SEQ ID NO:22:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: unknown to applicant ( i i ) MOLECULE TYPE: Other nucleic acid ( i i i ) HYPOTHETICAL: no ( x i ) SEQUENCE DESCRIPTION: SEQ ID NO:22:

```
CTCGCTCACT AATGAA                                                             16
```

( 2 ) INFORMATION FOR SEQ ID NO:23:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: unknown to applicant ( i i ) MOLECULE TYPE: Other nucleic acid ( i i i ) HYPOTHETICAL: no ( x i ) SEQUENCE DESCRIPTION: SEQ ID NO:23:

```
CTCGCTCACA AATACCACTA ATGAA                                                   25
```

( 2 ) INFORMATION FOR SEQ ID NO:24:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: unknown to applicant ( i i ) MOLECULE TYPE: Other nucleic acid ( i i i ) HYPOTHETICAL: no ( x i ) SEQUENCE DESCRIPTION: SEQ ID NO:24:

ACCGTTCTGA CTAGTAAATA CCGTTAATGA 30

( 2 ) INFORMATION FOR SEQ ID NO:25:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: unknown to applicant ( i i ) MOLECULE TYPE: Other nucleic acid ( i i i ) HYPOTHETICAL: no ( x i ) SEQUENCE DESCRIPTION: SEQ ID NO:25:

GGAGGTTAAT TAATGCTGTC TCCTGCAGAT 30

( 2 ) INFORMATION FOR SEQ ID NO:26:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: unknown to applicant ( i i ) MOLECULE TYPE: Other nucleic acid ( i i i ) HYPOTHETICAL: no ( x i ) SEQUENCE DESCRIPTION: SEQ ID NO:26:

CTGGTGGGTA AAGTTCTGGT TTGCGTTCTG 30

( 2 ) INFORMATION FOR SEQ ID NO:27:

( i ) SEQUENCE CHARACTERISTICS:
        ( A ) LENGTH: 50
        ( B ) TYPE: nucleic acid
        ( C ) STRANDEDNESS: single
        ( D ) TOPOLOGY: unknown to applicant ( i i ) MOLECULE TYPE: Other nucleic acid ( i i i ) HYPOTHETICAL: no ( x i ) SEQUENCE DESCRIPTION: SEQ ID NO:27:

CTAGTAAATA CCGATCGGGT GGCTCTGGCG GTTCTGTTCT GTCTCCTGCA 50

( 2 ) INFORMATION FOR SEQ ID NO:28:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: unknown to applicant ( i i ) MOLECULE TYPE: Other nucleic acid ( i i i ) HYPOTHETICAL: no ( x i ) SEQUENCE DESCRIPTION: SEQ ID NO:28:

GGAGACAGAA CAGAACCGCC AGAGCCACCC GATCGGTATT TA 42

( 2 ) INFORMATION FOR SEQ ID NO:29:

( i ) SEQUENCE CHARACTERISTICS:

-continued (A) LENGTH: 67
                (B) TYPE: nucleic acid
                (C) STRANDEDNESS: single
                (D) TOPOLOGY: unknown to applicant (ii) MOLECULE TYPE: Other nucleic acid (iii) HYPOTHETICAL: no (xi) SEQUENCE DESCRIPTION: SEQ ID NO:29:

GGCCGCCTTA AGTACCCGGG TTTCTGCAGA AAGCCCGCCT AATGAGCGGG                    50

CTTTTTTTTC CTTAGGG                                                        67

(2) INFORMATION FOR SEQ ID NO:30:

(i) SEQUENCE CHARACTERISTICS:
                (A) LENGTH: 67
                (B) TYPE: nucleic acid
                (C) STRANDEDNESS: single
                (D) TOPOLOGY: unknown to applicant (ii) MOLECULE TYPE: Other nucleic acid (iii) HYPOTHETICAL: no (xi) SEQUENCE DESCRIPTION: SEQ ID NO:30:

GATCCCCTAA GGAAAAAAAA GCCCGCTCAT TAGGCGGGCT TTCTGCAGAA                    50

ACCCGGGTAC TTAAGGC                                                        67

MODIFIED HEMOGLOBIN-LIKE COMPOUNDS

CROSS REFERENCE TO RELATED APPLICATION

This application is a continuation-in-part of U.S. application Ser. No. 08/240,712 issued as U.S. Pat. No. 5,599,907 on Feb. 4, 1997, having a U.S. Ser. No. 08/240,712, a national entry date of May 9, 1994, and filed on Nov. 6, 1992 as PCT Application No. PCT/US93/09752, which is incorporated herein by reference in its entirety.

BACKGROUND OF THE INVENTION

The present invention is directed to modified hemoglobin-like compounds, and more particularly to modified hemoglobin-like polypeptides and proteins.

Hemoglobin ( referred to herein as "Hb" or "Hgb") is the oxygen-carrying component of blood. Hemoglobin circulates through the bloodstream inside small enucleate cells called erythrocytes (red blood cells). Hemoglobin is a protein constructed from four associated polypeptide chains, and bearing prosthetic groups known as hemes. The erythrocyte helps maintain hemoglobin in its reduced, functional form. The heme iron atom is susceptible to oxidation, but may be reduced again by one of two enzyme systems within the erythrocyte, the cytochrome $b_5$ and glutathione reduction systems.

Hemoglobin binds oxygen at a respiratory surface (skin, gills, trachea, lung, etc.) and transports the oxygen to inner tissues, where it is released and used for metabolism. In nature, low molecular weight hemoglobins (16–120 kilodaltons) tend to be enclosed in circulating red blood cells, while the larger polymeric hemoglobins circulate freely in the blood or hemolymph.

The structure of hemoglobin is well known as described in Bunn & Forget, eds., *Hemoglobin: Molecular, Genetic and Clinical Aspects* (W.B. Saunders Co., Philadelphia, Pa.: 1986) and Fermi & Perutz "Hemoglobin and Myoglobin," in Phillips and Richards, *Atlas of Molecular Structures in Biology* (Clarendon Press: 1981).

About 92% of normal adult human hemolysate is Hb $A_o$ (designated alpha2 beta2 because it comprises two alpha and two beta chains). The amino acid sequences of the alpha and beta globin polypeptide chains of Hb A is given in Table 1 of PCT Publication No. WO 93/09143. The wild-type alpha chain consists of 141 amino acids. The iron atom of the heme (ferroprotoporphrin IX) group is bound covalently to the imidazole of His 87 (the "proximal histidine"). The wild-type beta chain is 146 residues long and heme is bound to it at His 92. Apohemoglobin is the heme-free analogue of hemoglobin, which exists predominantly as the $\alpha\beta$-globin dimer.

The human alpha and beta globin genes reside on chromosomes 16 and 11, respectively. Bunn and Forget, infra at 172. Both genes have been cloned and sequenced, Liebhaber, et al., PNAS 77: 7054–58 (1980) (alpha-globin genomic DNA); Marotta, et al., J. Biol. Chem., 252: 5040–53 (1977) (beta globin cDNA); Lawn, et al., Cell, 21:647 (1980) (beta globin genomic DNA).

Hemoglobin exhibits cooperative binding of oxygen by the four subunits of the hemoglobin molecule (two alpha-globins and two beta-globins in the case of Hgb A), and this cooperativity greatly facilitates efficient oxygen transport. Cooperativity, achieved by the so-called heme-heme interaction, allows hemoglobin to vary its affinity for oxygen. Hemoglobin reversibly binds up to four moles of oxygen per mole of Hgb.

Oxygen-carrying compounds are frequently compared by means of a device known as an oxygen dissociation curve. This curve is obtained when, for a given oxygen carrier, oxygen saturation or content is graphed against the partial pressure of oxygen. For Hgb, the percentage of saturation increases with partial pressure according to a sigmoidal relationship. The $P_{50}$ is the partial pressure at which the oxygen-carrying solution is half saturated with oxygen. It is thus a measure of oxygen-binding affinity; the higher the $P_{50}$, the more loosely the oxygen is held.

When the oxygen dissociation curve of an oxygen-carrying solution is such that the $P_{50}$ is less than that for whole blood, it is said to be "left-shifted."

The oxygen affinity of hemoglobin is lowered by the presence of 2, 3-diphosphoglycerate (2,3-DPG), chloride ions and hydrogen ions. For example, respiring tissue releases carbon dioxide into the blood and lowers its pH (i.e. increases the hydrogen ion concentration), thereby increasing the amount of oxygen that dissociates from hemoglobin and diffuses into individual cells.

The ability of hemoglobin to alter its oxygen affinity under physiological conditions, increasing the efficiency of oxygen transport around the body, is dependent on the presence of the metabolite 2,3-DPG. Inside the erythrocyte 2, 3-DPG is present at a concentration nearly as great as that of hemoglobin itself. In the absence of 2,3-DPG "conventional" hemoglobin binds oxygen very tightly at physiological oxygen partial pressures and would release little oxygen to respiring tissue.

It is not always practical or safe to transfuse a patient with donated blood. In these situations, use of a red blood cell ("RBC") substitute is desirable. The product must effectively transport $O_2$, just as do red blood cells. ("Plasma expanders", such as dextran and albumin, do not transport oxygen.) The two types of oxygen-carrying substitutes that have been studied most extensively are hemoglobin solutions and fluorocarbon emulsions.

It is clear from the above considerations that free native hemoglobin A, injected directly into the bloodstream, would not support efficient oxygen transport about the body. The essential allosteric regulator 2,3-DPG is not present in sufficient concentration in the plasma to allow hemoglobin to release much oxygen at venous oxygen tension.

Nonetheless, solutions of conventional hemoglobin have been used as RBC substitutes. The classic method of preparing hemoglobin solutions employs outdated blood. The red cells are lysed and cellular debris is removed, leaving what is hopefully "stromal-free hemoglobin" (SFH).

Several basic problems have been observed with this approach. The solution must be freed of any toxic components of the red cell membrane without resorting to cumbersome and tedious procedures which would discourage large-scale production.

Second, as expected, such solutions are "left-shifted" (lower $P_{50}$) as compared to whole blood. As a result, the oxygen affinity is too high to unload enough oxygen into the tissues.

Third, SFH has only a limited half-life in the circulatory system. This is because oxy Hb partially dissociates into a dimer ($\alpha\beta$) that is rapidly cleared from the blood by glomerular filtration and binding to circulating haptoglobulin. If large amounts of soluble hemoglobin are introduced into the circulation, glomerular filtration of the dimers may lead to a protein and iron load on the kidney capable of causing renal damage.

Finally, SFH has a high colloid osmotic pressure (COP). Thus, administration of SFH in a dose that would have the same oxygen-carrying capacity as a unit of packed red blood cells is inadvisable, since the high osmotic pressure (60 mm Hg) would cause a massive influx of water from the cells into the bloodstream, thus dehydrating the patient's tissues. This consideration limits the dose of SFH to that which provides a final concentration of about 6–8 gm Hb/dl.

Many mutant forms of normal Hb Ao are also known. Several mutants are identified in Table 400 of PCT Publication No. WO 93/09143. There are also a few known naturally occurring mutants of human hemoglobin in which a cysteine residue is substituted for another residue of normal hemoglobin Ao. Harris et al., Blood 55(1):131–137 (1980)(Hemoglobin Nigeria); Greer et al., Nature [New Biology], 230:261–264 (1971) (Hemoglobin Rainier). Hemoglobin Nunobiki ($\beta$141 Drg→Cys) also features a non-polymerizing cysteine substitution. In both Hb Rainier and Hb Nunobiki, the new cysteine residues are on the surface of the moiety.

Three other human mutants are known that polymerize as a result of formation of intermolecular (first tetramer to second tetramer) disulfide bridges. Tondo, Biochem. biophys. Acta, 342:15–20 (1974) and Tondo, An. Acad. Bras. Cr., 59:243–251 (1987) describe one such mutant known as Hb Porto Alegre. Hb Mississippi is characterized by a cysteine substitution in place of Ser CD3(44)$\beta$ and is believed to be composed of ten or more hemoglobin tetramers according to Adams et al., Hemoglobin. 11(5):435–542 (1987). Hemoglobin Ta Li is characterized by a $\beta$83j(EF7) Gly→Cys mutation, which showed slow mobility in starch gel electrophoresis, indicating that it too was a polymer.

Polymeric hemoglobins have also been reported in various vertebrates and invertebrates. Murine polymeric hemoglobins are described in Bonaventura & Riggs, Science, 149:800–802 (1967); and Riggs, Science, 147:621–623 (1965). A polymerizing hemoglobin variant is reported in Takenaka et al., Biochem. Biophys. Acta, 492:433–444 (1977); Ishimoto et al., I. Anthrop. Soc. Nippon, 83(3):233–243 (1975). Both amphibians and reptiles also possess polymerizing hemoglobins. Tam et al., J. Biol. Chem., 261:8290–94 (1986).

The extracellular hemoglobin of the earthworm (Lumbricus terrestris) has a complex structure. There are twelve subunits, each being a dimer of structure $(abcd)_2$ where "a", "b", "c", and "d" denote the major heme containing chains. The "a", "b", and "c" chains form a disulfide-linked trimer. The whole molecule is composed of 192 heme-containing chains and 12 non-heme chains, and has a molecular weight of 3800 kDa. Other invertebrate hemoglobins are also large multi-subunit proteins.

The brine shrimp Artemia produces three polymeric hemoglobins with nine genetically fused globin subunits. Manning, et al., Nature, 348:653 (1990). These are formed by variable association of two different subunit types, a and b. Of the eight intersubunit linkers, six are 12 residues long, one is 11 residues and one is 14 residues.

Non-polymerizing crosslinked hemoglobins have also been artificially produced. For example, hemoglobin has been altered by chemically crosslinking the alpha chains between the Lys99 of alpha1 and the Lys99 of alpha2. Walder, U.S. Pat. Nos. 4,600,531 and 4,598,064; Snyder, et al., PNAS (USA) 84: 7280–84 (1987); Chaterjee, et al., J. Biol. Chem., 261: 9927–37 (1986). The beta chains have also been chemically crosslinked. Kavanaugh, et al., Biochemistry, 27: 1804–8( 1988). U.S. Pat. No. 5,028,588 suggests that the T state of hemoglobin may be stabilized by intersubunit (but intratetrameric) disulfide crosslinks resulting from substitution of cysteine residues for other residues.

Hemoglobin has also been artificially crosslinked to form polymers. For example, U.S. Pat. No. 4,001,401, U.S. Pat. No. 4,001,200, and U.S. Pat. No. 4,053,590 all relate to polymerization of red blood cell-derived hemoglobin by chemical crosslinking. The crosslinking is achieved with the aid of bifunctional or polyfunctional crosslinking agents, especially those reactive with exposed amino groups of the globin chains. The result of the crosslinking reaction is a polydisperse composition of covalently cross-linked aggregates.

Bonhard, U.S. Pat. No. 4,336,248 discloses chemical crosslinking of hemoglobin molecules to each other, or to serum proteins such as albumin.

Bonhard, U.S. Pat. No. 4,777,244 sought to stabilize the dialdehyde-cross-linked hemoglobins, which tended to polymerized further while in storage, by adding a reducing agent to stabilize the azomethine bond.

Bucci, U.S. Pat. No. 4,584,130, at col. 2, comments that "the polyhemoglobin reaction products are a heterogeneous mixture of various molecular species which differ in size and shape. The molecular weights of these polyhemoglobins range from 64,500 to 600,000 Daltons. The separation of individual molecular species from the heterogeneous mixture is virtually impossible. In addition, although longer retention times in vivo are obtained using polyhemoglobins, the oxygen affinity thereof is higher than that of stroma-free hemoglobin."

It is well recognized, however, that random polymerization is difficult to control and that a number of different polymers can be obtained, commonly between two and ten tetramers per polymer. For example, according to Tye, U.S. Pat. No. 4,529,719, polymerized pyridoxylated hemoglobin has "a profound chemical heterogeneity making it difficult to study as a pharmaceutical agent."

Genetic fusion has also been used as a means for linking proteins generally. Genes may be fused together by removing the stop codon of the first gene, and joining it in phase to the second gene. Parts of genes may also be fused, and spacer DNAs which maintain phase may be interposed between the fused sequences. The product of a fused gene is a single polypeptide, not a plurality of polypeptides as is expressed by a polycistronic operon. Different genes have been fused together for a variety of purposes.

The use of linker DNA sequences to join two different DNA sequences is known. These linkers are used to provide restriction sites for DNA cleavage, or to encode peptides having a unique character that facilitates purification of the encoded fusion protein or a fragment thereof. See, e.g., Rutter, U.S. Pat. No. 4,769,326.

Hoffman, et al., WO88/09179 describes the production of globin domains fused to leader peptides which are cleaved prior to processing the final product. Anderson et al., WO 93/09143 describe the production, in bacteria and yeast, of hemoglobin and analogues thereof. The disclosed analogues including hemoglobin proteins in which one of the component polypeptide chains consists of two alpha or two beta globin amino acid sequences covalently connected by peptide bonds, preferably through an intermediate linker of one or more amino acids, without branching. In normal hemoglobin, the alpha and beta globin subunits are non-covalently bound.

Correlations of molecular weight with serum half life for various proteins, such as IL-2, demonstrate that a significantly longer half life may be expected as the molecular weight of a protein increases, particularly above the renal filtration limit of 50–70 kDa. In addition, the use of crosslinkers that can inhibit the degradation of hemoglobin tetramers into dimers that are readily cleared can also lead to increased serum half life. Accordingly, a need exists for additional hemoglobin-like compounds having these desired characteristics. The present invention satisfies this need and provides related advantages as well.

SUMMARY OF THE INVENTION

Figure 1A:
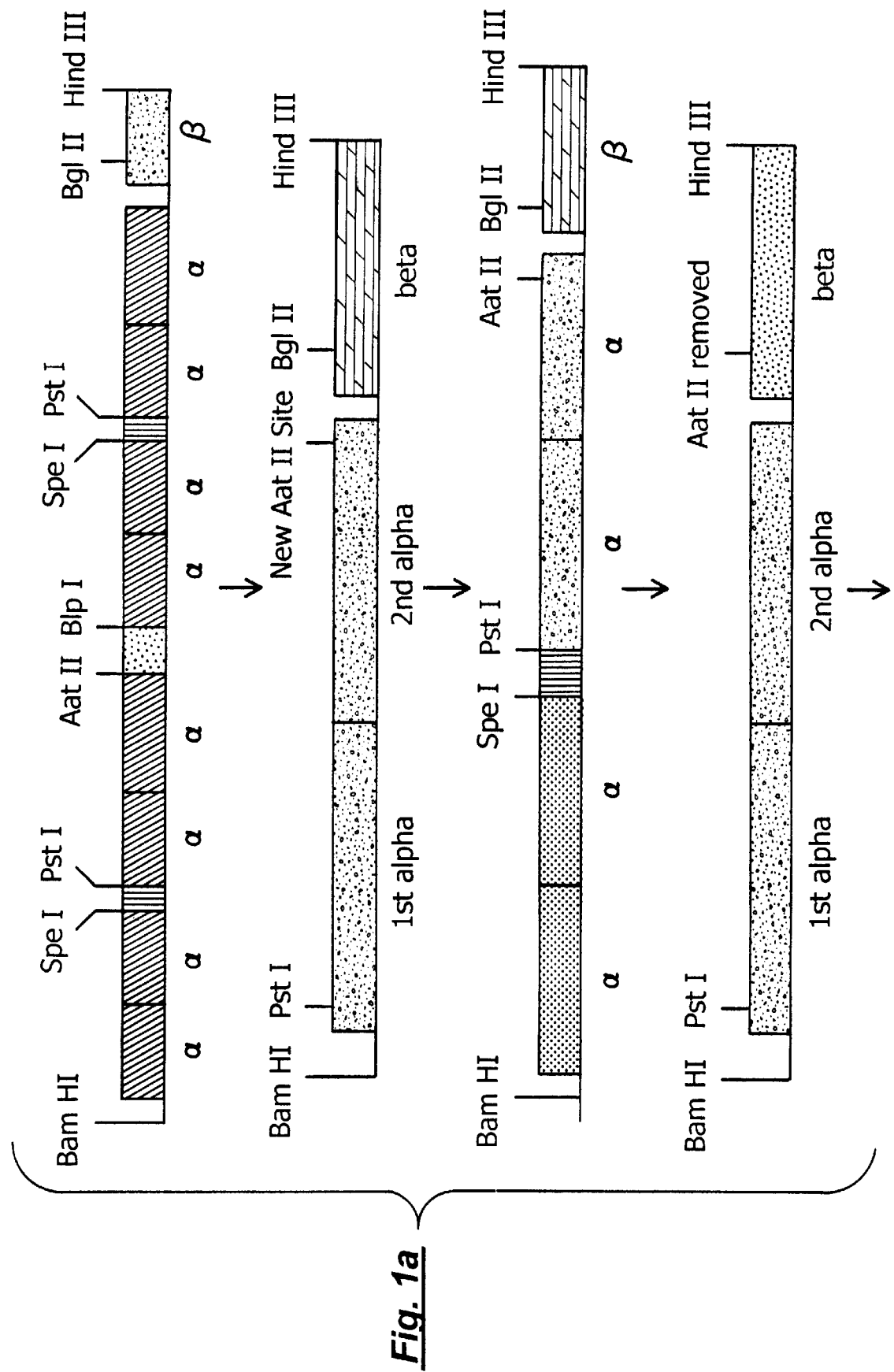
FIG. 1 is a schematic diagram of fragments useful for making tetra di-alpha globin polypeptides.

The present invention relates to modified hemoglobin-like compounds. In one aspect, the invention is directed to globin-like polypeptides having multiple di-alpha domains. Such polypeptides can contain two di-alpha domains, also referred to herein as "di di-alpha" domains, or more. These globin-like polypeptides can be linked by a peptide linker having at least five amino acids between the di-alpha domains, preferably at least seven amino acids. Preferably, the linkers are encoded by a peptide linker having Ser-Gly-Gly as a repeat unit, such as the amino acid sequences: Ser-Gly-Gly-Ser-Gly-Gly-Ser (SEQ.ID.NO.1); Gly-Gly-Ser-Gly-Gly-Ser-Gly-Gly-Ser-Gly-Gly-Ser-Gly-Gly (SEQ.ID.No. 2) and Ser-Gly-Gly-Ser-Gly-Gly-Ser-Gly-Gly-Ser-Gly-Gly-Ser-Gly-Gly-Ser (SEQ.ID.No. 3). The globin-like polypeptides can be recombinantly expressed in a host cell, such as $E.\ coli$.

The invention also relates to nucleic acid molecules having a nucleic acid sequence encoding such globin-like polypeptides. In one embodiment, the nucleic acid molecules encode a globin-like polypeptide having two di-alpha domains and a separate polypeptide having a single beta domain or a di-beta domain.

In another aspect, the present invention also provides multimeric hemoglobin-like proteins in which a first hemoglobin-like moiety is directly attached to two or more other hemoglobin-like moieties. Compositions containing such multimeric hemoglobin-like proteins are also provided.

In a further aspect, the present invention relates to methods for making the multimeric hemoglobin-like proteins. The methods are accomplished by:

(a) obtaining a first hemoglobin-like moiety having amino acids capable of attaching to one end of a heterobifunctional linker to form a core hemoglobin-like moiety;

(b) obtaining at least two other hemoglobin-like moieties having an amino acid capable of attaching to the other end of the heterobifunctional linker;

(c) contacting the heterobifunctional linker to the first hemoglobin-like moiety; and (d) adding the other hemoglobin-like moieties to form the multimeric emoglobin-like protein.

DETAILED DESCRIPTION OF THE INVENTION

The present invention generally relates to hemoglobin-like compounds comprised of novel globin-like polypeptides or hemoglobin-like proteins. These compounds contain various modifications to the naturally-occurring hemoglobins, particularly human Hb Ao.

As described above, most naturally-occurring human hemoglobins are constructed of four polypeptide chains: two chains containing identical alpha domains and two chains containing identical beta domains. The novel globin-like polypeptides of the present invention, however, contain at least two di-alpha domains in a single polypeptide chain. A "di-alpha domain" consists of two alpha domains (or polypeptide sequences) connected between the C-terminus of a first alpha domain and the N-terminus of a second alpha domain as described in PCT Publication No. WO 93/09143, incorporated herein by reference. Thus, the novel globin-like polypeptides have as a minimum four alpha domains per polypeptide.

As used herein, the term "globin-like polypeptide" means a polypeptide having a domain that is substantially homologous with a globin subunit of a naturally occurring hemoglobin. For example, a globin-like polypeptide containing two di alpha domains means that each of the four alpha domains is substantially homologous to a native alpha globin or a mutant thereof differing from the native sequence by one or more substitutions, deletions or insertions, while remaining substantially homologous with the native alpha globin and retaining its ability to associate with a beta globin. As used herein, the term "alpha domain" is intended to include but not be limited to naturally occurring alpha globins, including normal human alpha globin, and mutants thereof. A "beta domain" is analogously defined. Subunits of vertebrate and invertebrate hemoglobins or mutants thereof which are sufficiently homologous with human alpha or beta globin are embraced by the terms "alpha or beta domains." For example, the subunits of bovine hemoglobin are within the scope of these terms.

In determining whether an alpha or beta globin contemplated by the present invention is substantially homologous to a particular wild-type alpha or beta globin, sequence similarity is an important but not exclusive criterion. Sequence similarity may be determined by conventional algorithms, which typically allow introduction of a small number of gaps in order to achieve the best fit. An alpha domain contemplated for use in the present invention will typically have at least about 75% sequence identity with wild-type human alpha globin, and greater homology with human alpha globin than with human beta globin. However, a polypeptide having an alpha domain of lesser sequence identity may still be considered "substantially homologous" with a wild-type alpha globin if it has a greater sequence identity than would be expected from chance and also has the characteristic higher structure (e.g., the "myoglobin fold") of alpha globin.

Mutations can be introduced to alter the oxygen affinity (or its cooperativity, or its dependence on pH, salt, temperature, or other environmental parameters) or stability (to heat, acid, alkali, or other denaturing agents) of the hemoglobin, to facilitate genetic fusion or crosslinking, or to increase the ease of expression and assembly of the individual chains. Guidance as to certain types of mutations is provided, for example, in U.S. Pat. No. 5,028,588 and PCT Publication No. WO 93/09143, both incorporated herein by reference. The present invention further includes molecules which depart from those taught herein by gratuitous mutations that do not substantially affect biological activity.

The di-alpha domains of the novel globin-like polypeptides can be connected by various means known in the art. For example, the domains can be coupled by a peptide linker between any two di-alpha domains. A discussion of the distances are also provided in WO 93/09143, incorporated herein by reference. With knowledge of these distances, one skilled in the art can readily determine, for example through molecular modeling, the useful lengths of suitable peptide linkers. Particularly useful peptide linkers have at least five amino acids, preferably at least seven amino acids. The peptide linker can have an amino acid sequence that contains Ser-Gly-Gly as a repeating unit, as in the following illustrative amino acid sequence: Ser-Gly-Gly-Ser-Gly-Gly-Ser (SEQ.ID.NO. 1). Examples of other amino acid sequences useful as peptide linkers containing this repeating unit include: Gly-Gly-Ser-Gly-Gly-Ser-Gly-Gly-Ser-Gly-Gly-Ser-Gly-Gly (SEQ.ID.No. 2) and Ser-Gly-Gly-Ser-Gly-Gly-Ser-Gly-Gly-Ser-Gly-Gly-Ser-Gly-Gly-Ser (SEQ.ID.No. 3).

The multiple di-alpha domains and the peptide linkers of the globin-like polypeptides can be genetically fused through recombinant methods known in the art or as described, for example, in WO 93/09143 or in the Examples below. The preparation of a single di-alpha globin as an intermediate product is also described in this publication.

The globin-like polypeptides can be used to prepare hemoglobin-like pseudomers. Such pseudomeric Hb-like proteins are described in WO 93/09143. Pseudomeric hemoglobin-like proteins have at least one more domain than the number of polypeptide chains, i.e., at least one polypeptide chain contains two or more globin-like domains.

It is also possible to introduce asymmetric cysteine residues into one alpha subunit of a di-alpha domain or one alpha subunit of a di di-alpha domain or larger di-alpha domains to prepare other pseudomeric hemoglobin-like proteins. The asymmetric cysteine residues can then be used to form direct disulfide bridges connecting the di-alpha domains or crosslinked by coupling reagents specific for cysteine residues to produce the larger pseudomeric Hb proteins.

The hemoglobin-like pseudomers can be purified by any suitable purification method known to those skilled in the art. Useful purification methods for the hemoglobin-like proteins of the present invention are taught in PCT Publication WO 95/14038, incorporated herein by reference. Briefly, the methods described therein involve an immobilized metal affinity chromatography resin charged with a divalent metal ion such as zinc, followed by a Q-sepharose anion exchange column. According to this publication, the solution containing the desired Hb-containing material to be purified can first be heat treated to remove protoporphryin IX-containing Hb. This basic purification method can be further followed by a sizing column (S-200), then another anion exchange column. The resulting solution can then be buffer exchanged to the desired formulation buffer.

The invention further provides nucleic acids encoding the novel polypeptides of the present invention. Those skilled in the art can readily derive a desired nucleotide sequence based on the knowledge of published nucleotide or amino acid sequences of known hemoglobin subunits with selection of codons and control elements specific for the organism used for expression, using methods known in the art. For example, the amino acid sequence of the di-alpha domain and the beta domain of a synthetic hemoglobin can be used to derive the nucleic acids of the present invention, both of which are identified in FIG. 12 of PCT Publication WO 90/13645, incorporated herein by reference, with the following corrections to the nucleotide sequence: bases 55, 56 and 57 (codon 19) should read GCG and bases 208 and 209 (the first two bases of codon 70) should read GC. The following changes to the amino acid sequence of this figure would yield the pseudotetramer, rHb1.1: the gly-gly bridge at residues 142 and 143 of the di-alpha domain can be changed to a single gly residue bridging $\alpha_1$ and $\alpha_2$ domains; residues 54 and 97 of the di-alpha domain should read Gln; residue 70 of the beta subunit should read Asn; and residue 107 of the beta subunit should read Lys. The pseudotetramer, rHb1.1 is also described in Looker et al., *Nature*, 356:258–260 (1992), incorporated herein by reference.

The nucleic acids of the present invention can be used to construct plasmids to be inserted into appropriate recombinant host cells according to conventional methods or as described in the Examples below. Any suitable host cell can be used to express the novel polypeptides. Suitable host cells include, for example, bacterial, yeast, mammalian and insect cells. *E. coli* cells are particularly useful for expressing the novel polypeptides. Preferably, when multiple subunits are expressed in bacteria, it is desirable, but not required, that the subunits be co-expressed in the same cell polycistronically as described in WO 93/09143. The use of a single promoter is preferable in *E. coli* to drive the expression of the genes encoding the desired proteins.

The present invention is also directed to novel multimeric hemoglobin-like proteins containing at least three hemoglobin-like moieties, of which one is directly attached to the other moieties. The term "hemoglobin-like moiety" includes tetramers having four globin-like domains composed of two alpha domains and two beta domains and pseudomeric hemoglobin-like proteins as previously defined. The hemoglobin-like moiety that is directly attached to the other hemoglobin-like moieties is referred to herein as the "core hemoglobin-like moiety", or "core moiety," while the other hemoglobin-like moieties are referred to as the surrounding hemoglobin-like moieties or "surrounding moieties."

In one embodiment, the core moiety is different from the surrounding hemoglobin-like moieties, which in turn can be the same or different from each other. Such multimeric hemoglobin-like proteins are referred to as heteromultimeric hemoglobin-like proteins (or heteromers). For example, the core moiety can be rHb1.1, while the surrounding moieties can be mutants referred to as K158C. The pseudotetramer, rHb1.1, is described in WO 90/13645, incorporated herein by reference. K158C is a mutant moiety of rHb1.1 and is composed of three polypeptides, one containing two alpha domains (a di-alpha) and the other two each containing a single beta domain. A single lysine to cysteine substitution in the second alpha domain of the di-alpha component appears at amino acid residue 158 of the K158C di-alpha sequence. A general method for obtaining a moiety having one or more asymmetrical cysteine mutations and the desirability of such asymmetrical crosslinked mutants are provided in WO 93/09143, which is specifically incorporated herein by reference. The publication also provides guidance for selecting other candidate sites for substitution on the alpha or beta domains.

The core and surrounding moieties can be directly attached by any means known in the art, including without limitation the use of chemical crosslinkers. For heteromultimer hemoglobin-like proteins, a heterobifunctional chemical crosslinker is preferred, such as a succinimidyl 4-(N-maleimidomethyl)cyclohexane-1-carboxylate (SMCC). Other useful heterobifunctional crosslinkers are described in WO 93/09143, incorporated herein by reference. For example, the succinimide of SMCC can be used to attach to the lysine residue of the non-cysteine mutated moieties, such as rHb1.1, while the maleiimide can be used to attach to the cysteine of the mutated moiety, such as K158C. By first reacting linkers with the core moiety, then adding the desired amount of cysteine-containing mutant, various forms of these multimeric hemoglobin-like proteins can be made, for example a trimeric, tetrameric, pentameric and higher order multimeric proteins. Factors that constrain the number of hemoglobin-like moieties that can be attached to the core moiety include steric hindrance as additional surrounding moieties are added and the number of residues that are available for attaching to the crosslinkers. Methods for identifying and using such crosslinkers are known to those skilled in the art or as described in the Examples below.

In a further embodiment, the core moiety and the surrounding moieties can be the same moiety, which is referred to herein as "homomultimeric hemoglobin-like proteins." An example is a homomultimeric Hb-like protein composed of only K158C mutants.

For making the multimeric hemoglobin-like proteins of this embodiment, the formation of substantial amounts of polymerized proteins is preferably avoided. Polymerized proteins contain Hb-like moieties that are indirectly attached to the core moiety through attachment to a surrounding moiety. Although any method known in the art can be used in which site specific attachment can be achieved, the present invention also provides methods for making homomultimeric hemoglobin-like proteins. These methods are accomplished by the use of a heterobifunctional crosslinker and borate.

Through the use of an appropriate amine/sulfhydryl heterobifunctional crosslinker, a desired hemoglobin-like moiety, for example, rHb1.1, can be modified so that it will subsequently react with several rHb1.1 molecules bearing surface Cys mutations as described in WO 93/09143. This reaction is achieved, for example, by first reacting amine functions on unmodified rHb1.1 with the succinimide moiety of the heterobifunctional crosslinker in a sodium borate buffer at pH 8.5. The intrinsic sulfhydryl groups of rHb1.1 are prevented from reacting by either their inaccessability or by complexation with borate. By using an appropriate concentration of crosslinker and reaction time, which can be determined empirically by those skilled in the art, the reaction with surface cys containing rHb1.1 (e.g., K158C) in subsequent steps yields an acceptable product in terms of apparent molecular weight and stability. The polymer formed is a distribution of apparent molecular weights. However, with certain moieties such as K158C as described in Example 10, the extent of initial activation with sulfo-SMCC and the site-directed nature of the reaction with K158C limits the molecular weight distribution to predominantly pentaHb. It is believed that the manipulation of reactivity, such as sulfhydryl reactivity, through reversible complexation with a suitable protective buffer, such as borate/boric acid for certain mutants, is a novel method for controlling reactivity, such as sulfhydryl reactivity, in forming the multimeric hemoglobin-like proteins of the present invention.

Accordingly, the present invention further provides methods for making a multimeric hemoglobin-like protein. The methods are accomplished by:

(a) obtaining a first hemoglobin-like moiety having an amino acid capable of attaching to one end of a heterobifunctional linker to form a core hemoglobin-like moiety;

(b) obtaining at least two other hemoglobin-like moieties having an amino acid capable of attaching to the other end of the heterobifunctional linker;

(c) contacting the heterobifunctional linker to the first hemoglobin-like moiety to form a linked moiety; and (d) contacting the other hemoglobin-like moieties to the linked moiety to form the multimeric hemoglobin-like protein.

The invention further provides compositions containing the novel multimeric hemoglobin-like proteins of the present invention and the globin-like polypeptides, including proteins containing such polypeptides. In compositions containing the multimeric hemoglobin-like proteins, a polydisperse composition containing various multimeric proteins can be obtained, i.e., differing species of trimerics, tetramerics, pentamerics and so forth. In addition, these compositions containing the multimeric hemoglobin-like proteins are preferably substantially free of polymerized proteins, although need not be completely free depending on the intended use of the desired proteins. As used in this context, "substantially free" means the presence of polymerized proteins will not adversely affect the desired function of the multimeric hemoglobin-like proteins.

The hemoglobin-like proteins and compositions containing the globin-like polypeptides or the multimeric hemoglobin-like proteins can be used for a number of purposes.

In one embodiment, the proteins or compositions can be formulated for use in therapeutic applications. For example, the formulations of the present invention can be used in compositions useful as substitutes for red blood cells in any application that red blood cells are used. Such compositions of the instant invention formulated as red blood cell substitutes can be used for the treatment of hemorrhage where blood volume is lost and both fluid volume and oxygen carrying capacity must be replaced. Moreover, because the compositions of the instant invention can be made pharmaceutically acceptable, the formulations of the instant invention can be used not only as blood substitutes that deliver oxygen but also as simple volume expanders that provide oncotic pressure due to the presence of the large hemoglobin protein molecule.

A typical dose of hemoglobin as a blood substitute is from 10 mg to 5 grams or more of extracellular hemoglobin per kilogram of patient body weight. Thus, a typical dose for a human patient might be from less than a gram to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, the particular purpose to be achieved according to the determination of those skilled in the art.

Administration of extracellular hemoglobin can occur for a period of seconds to hours depending on the purpose of the hemoglobin usage. For example, as a blood delivery vehicle, the usual time course of administration is as rapid as possible. Typical infusion rates for hemoglobin solutions as blood replacements can be from about 100 ml to 3000 ml/hour. However, when used to stimulate hematopoiesis, administration can last only seconds to five minutes and therefore administration rates can be slower because the dosage of hemoglobin is much smaller than dosages that can be required to treat hemorrhage.

In a further embodiment, the formulation of the instant invention can be used to treat anemia, both by providing additional oxygen carrying capacity in a patient that is suffering from anemia, and by stimulating hematopoiesis. In addition, because the distribution of the hemoglobin in the vasculature is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation and the like.

The compositions of the instant invention can also be used as replacement for blood that is removed during surgical procedures where the patient's blood is removed and saved for reinfusion at the end of surgery or during recovery (acute normovolemic hemodilution or hemoaugmentation).

For use as an oxygen carrier, the hemoglobin-like proteins containing the novel globin-like polypeptides or the multimeric proteins of the present invention preferably have a $P_{50}$ of 2 to 75 torr, more preferably 24 to 32 torr, at 37° C., in blood and also exhibit cooperativity to some degree. The proteins desirably have an intravascular retention at least comparable to that of normal human hemoglobin administered as a blood substitute.

Because the hemoglobin of the instant invention can bind nitric oxide and other non-oxygen ligands as well as oxygen, the formulations of the instant invention are also useful for the binding or delivery of nitric oxide or non-oxygen ligands. These non-oxygen ligands can be bound or delivered both in vivo or in vitro. For example, the hemoglobin of the instant invention may be used to remove excess nitric oxide from a living system. Excess nitric oxide has been implicated in conditions ranging from hypotension to septic shock. Likewise, nitric oxide or other non-oxygen ligands may be delivered to a system to alleviate a disease condition. For example, nitric oxide could be delivered to the vasculature to treat hypertension. Other therapeutic uses of the instant invention can include drug delivery and in vivo imaging.

The proteins and compositions of the present invention can also be used for a number of in vitro applications. For example, the delivery of oxygen by the proteins of the instant invention alone or in a composition can be used for the enhancement of cell growth in cell culture by maintaining oxygen levels in vitro. Moreover, the hemoglobin of the instant invention can be used to remove oxygen from solutions requiring the removal of oxygen, and as reference standards for analytical assays and instrumentation.

The following Examples are intended to illustrate, but not limit, the present invention.

EXAMPLE 1

Production of Protein Solution Containing Modified Hemoglobin

A. Construction of a Bacterial System for the Recombinant Production of Modified rHb1.1

Modified hemoglobins were produced by fermentation of the E. coli strain 1661 carrying the plasmid pSGE705. Construction of pSGE705 is described below.

Strain SGE661 carrying the plasmid pSGE705 is SGE1662.

Materials. pBR322, pUC19 and pNEB193 were purchased from New England Biolabs, Beverly, Mass. Oligonucleotides were synthesized on an Applied Biosystems DNA Synthesizer Model 392. The oligonucleotides used in preparing pSGE705 are listed in Table 3. Restriction endonucleases were purchased from New England Biolabs, Beverly, Mass. and used according to manufacturer's specifications. T4 DNA Ligase was purchased from either New England Biolabs, Beverly, Mass. or Gibco-BRL (Gaithersburg, Mass.) and used according to manufacturer's specifications. Pfu polymerase was purchased from Stratagene (La Jolla, Calif.) and used according to manufacturer's specifications.

Media used are described in J. H. Miller (*Experiments in Molecular Genetics*. Cold Spring Harbor Press, (1972) Cold Spring Harbor, N.Y.). and J. H. Miller (*A Short Course in Bacterial Genetics*. (1992) Cold Spring Harbor Press, Cold Spring Harbor, N.Y.). Acridine orange, ampicillin and kanamycin sulfate were purchased from Sigma Chemical Co. (St. Louis, Miss.). Tetracycline was purchased from Aldrich Chemicals (Milwaukee, Wis.).

Genetic and Molecular Biological Procedures. Standard bacterial genetic procedures are described in J. H. Miller (*Experiments in Molecular Genetics*. (1972) Cold Spring Harbor Press, Cold Spring Harbor, N.Y.) and J. H. Miller (*A Short Course in Bacterial Genetics*. (1992) Cold Spring Harbor Press, Cold Spring Harbor, N.Y.). Standard molecular biology procedures were performed as described by Sambrook (Sambrook et al., *Molecular Cloning*. (1989) Cold Spring Harbor Press, Cold Spring Harbor, N.Y.).

Plasmid DNA Transformation. DNA transformations were performed by the procedure described by Wensick (Wensick et al., (1974) Cell 3:315–325). Briefly, cells were grown to mid log phase and then pelleted, resuspended in an equal volume of 10 mM $MgSO_4$ and incubated on ice for 30 minutes. The cells were centrifuged and the pellet resuspended in ½ original volume of 50 mM $CaCl_2$ and placed on ice for 20 minutes. The cells were centrifuged again and then resuspended in 1/10 original volume of 50 mM $CaCl_2$. Plasmid DNA was added to the competent cells in a solution of 10 mM Tris-HCl pH 8.0, 10 mM $MgCl_2$ and 10 mM $CaCl_2$. The mixture was incubated on ice for 15 minutes and then incubated at 37° C. for 5 minutes. One milliliter of LB medium was added and the mixture incubated with shaking for 30–60 minutes. The culture was then centrifuged, resuspended in 0.1 ml of LB medium and plated on the appropriate selective medium.

Purification of DNA. DNA fragments were purified from an agarose gel using the Geneclean system. (Bio 101, Inc. La Jolla, Calif.; method provided with product.) PCR products were prepared and cleaved with restriction endonucleases using the Double Geneclean system. (Bio 101, Inc. La Jolla; method provided with product.) Briefly, the PCR product was purified away from the PCR primers, then the PCR product was cleaved with restriction endonudease(s) and purified from the restriction endonudease and buffer. The PCR product was then ready for a ligation reaction.

TABLE 1

Plasmids

| PLASMID | DESCRIPTION |
| --- | --- |
| pSGE1.1E4 | rHbl.1 expression plasmid containing di-alpha and beta genes |
| pSGE1.1E5 | like pSGE1.1E4 but ampicillin resistant instead of tetracydine resistant |
| pSGE490 | pUC19 lacI on a Bam HI-Hind III fragment |
| pSGE491 | pUCI9 α on an Eco RI-Xba I fragment |
| pSGE492 | pNEB193 Ptac-α |
| pSGE493 | pUC19 β on an Xba I-Hind III fragment |
| pSGE500 | pUC19 α β on a Bam HI-Hind III fragment |
| pSGE504 | pSELECT-1 replace Sty I with a Pme I site |
| pSGE505 | pSGE504 rrnB T1 transcriptional terminator in the Eco RI-Cla I sites |
| pSGE507 | ColE1 ori and tet, 2213 bp |
| pSGE509 | ColE1 ori tet lacI, 3425 bp |
| pSGES13 | ColE1 ori tet lacI α β, 4386 bp |
| pSGE515 | ColE1 ori tet lacI dia β, 4812 bp |

TABLE 1-continued

Plasmids

| PLASMID | DESCRIPTION |
|---|---|
| pSGE700 | pTZ18U + diα β from pSGE515 |
| pSGE705 | modified rHb1.1 expression plasmid, ColE1 ori, tet, lacI, di-alpha and beta genes |
| pTZ18U | a phagemid derivative of pUC19, for oligonucleotide directed mutagenesis |
| pDLII-91F | pGEM1 + α missing valine in 2nd position (Des-val) |
| pNEB193 | Like pUC19 but has more restriction sites in the multi cloning sites |
| pBR322 | ColE1 ori tet amp |
| pRG1 | pACYC177 lacI9 |

TABLE 2

Oligonucleotides

| OLIGO | SEQUENCE (5'-3') | DESCRIPTION |
|---|---|---|
| EV18 SEQ. ID #4 | CGGGAATACGGTCTAGATCATTAA CGGTATTTCGAAGTCAGAACG | C-term of α gene, Xba I site |
| EV27 SEQ. ID #5 | GATCCGAGCTGTTGACAATTAAT CATCGGCTCGTATAATGTGT GGAATTGTGACGGATAACAATTT CACACAGGAAATTAATTAATGCT GTCTCC | tac promoter sequence, Bam HI-Eag I sites |
| EV28 SEQ. ID #6 | GGCCGGAGACAGCATTAATTAAT TTCCTGTGTGAAATTGTTATCCGCTCAC AATTCCACACATTATACGAGCCGATGA TTAATTGTCAACAGCTCG | tac promoter sequence, Bam HI-Eag I sites, complement of EV27 |
| EV29 SEQ. ID #7 | TCGGATTCGAATTCCAAGCTGTTGG ATCCTTAGATTGAACTGTCTCCGGCCG ATAAAACCACCG | 5' end of α with Eco RI, Bam HI and Eag I sites |
| EV30 SEQ. ID #8 | CGGAAGCCCAATCTAGAGGAA ATAATATATGCACCTGACTCCG GAAGAAAAATCC | 5' end of β with Xba I site |
| EV31 SEQ. ID #9 | CCCGAAACCAAGCTTCATTAGTGA GCTAGCGCGTTAGCAACACC | 3' end of the β gene with Hind III site |
| MW007 SEQ. ID #10 | TTTAAGCTTCATTAGTGGTATT TGTGAGCTAGCGCGT | mutagenesis reverse primer replaces last three codons of β missing in pSGE515 |
| MW008 SEQ. ID #11 | CAGCATTAATTAACCTCCTTA GTGAAATTGTTATCCG | mutagenesis reverse primer to optimize α ribozyme binding site (RBS) |
| MW009 SEQ. ID #12 | GGTGCATATATTTACCTCCTT ATCTAGATCATTAACGGTATTTCG | mutagenesis reverse primer to optimize β RBS and remove second Bgl 11 site |
| TG14 SEQ. ID #13 | GGTTTAAACC | Pme I linker |
| TG59 SEQ. ID #14 | GGCGAATAAAAGCTTGCGGCCGCG TTGACACCATCGAATGGCGCAAAA CCTTTCGCGG- | Upstream of lacI gene, has a Hind III and a Not I site upstream of the promoter |
| TG60 SEQ. ID #15 | GGGCAAATAGGATCCAAAAAAAAG CCCGCTCATTAGGCGGGCTTTAT CACTGCCCGCTTTCCAGTCGGG | Downstream side of lacI gene with the trp transcriptional terminator and a Bam HI site |
| TG62 SEQ. ID #16 | CCCCGAAAAGGATCCAAGTA GCCGGCGGCCGCGTTCCACTG AGCGTCAGACCCC | upstream primer for pBR322 ori positions 3170–3148 with a Bam HI and |

TABLE 2-continued

Oligonucleotides

| OLIGO | SEQUENCE (5'-3') | DESCRIPTION |
| --- | --- | --- |
| TG63<br>SEQ. ID #17 | GGCGGTCCTGTTTAAACGCT<br>GCGCTCGGTCGTTCGGCTGCGG | a Not I site downstream primer for pBR322 ori positions 2380–2404 with a Pme I site |

Annealing of oligonucleotides. Complementary oligonucleotides were annealed according to the following procedure. Equimolar amounts of each oligonucleotide were mixed in 15–25 μl of 10 mM Tris-HCl pH 8.0/1 mM EDTA and incubated at 65° C. for 30 minutes. The sample was transferred to a 37° C. water bath for 30 minutes. Finally, the sample was incubated on ice for 60 minutes or in the refrigerator overnight.

Oligonucleotide directed mutagenesis. Oligonucleotide directed mutagenesis was performed with the Muta-gene phagemid in vitro mutagenesis kit (Bio-Rad, Hercules, Calif.) according to manufacturer's instructions which are based on the method of Kunkel (Kunkel, T. A. (1985) Proc. Natl. Acad. Sci. USA 82:488; Kunkel et al., (1987) Methods Enzymol. 154:367). The rHb1.1 region of pSGE515 was cloned into pTZ18U (Bio -Rad, Hercules, Calif. or U.S. Biochemical, Cleveland, Ohio) on a Bam HI-Hind III fragment to create pSGE700. Three oligonucleotides, MW007, MW008 and MW009 were used to simultaneously introduce multiple changes in a single reaction.

Preparation of pBR322 ori. PCR primers were designed to amplify the pBR322 origin of replication. These primers, TG62 and TG63, annealed to the positions 2380–2404 and 3170–3148 on the pBR322 DNA sequence (Sutcliffe, J. G. 1979. Cold Spring Harbor Symp. Quant. Biol. 43:77–90). The PCR product was digested with Not I and Pme I. The DNA fragment was purified according to the Geneclean procedure.

Preparation of tet gene fragment. The source for the tet gene was pSELECT-1 (Promega Corp., Madison, Wis.). This plasmid has a number of restriction endonuclease sites, such as Bam HI, Hind III, Sal I and Sph I removed from the tet gene (Lewis and Thompson (1993) Nucleic Acids Res. 18:3439–3443). A Pme I linker was inserted into the Sty I site of pSELECT-1. This plasmid was designated pSGE504. Oligonucleotides TG71 and TG72 were annealed and ligated to the Eco RI—Cla I fragment of pSGE504. This plasmid, pSGE505, was shown to have the expected restriction endonuclease sites and to have lost the sites present in the multicloning site of pSELECT-1. pSGE505 was digested with Not I and Pme I. The 1417 bp fragment was purified according to the Genedean protocol.

Preparation of lacI gene. The lacI gene was isolated by amplifying the gene sequence from pRG1 (a gift from R. Garcia, Dana-Farber Cancer Inst., Boston) that carried the lacI gene. The PCR primers, TG59 and TG60 were designed to generate a wild type lacI promoter (Farabaugh, P. J. (1978) Nature 274:765), upstream of the gene and to place the trp terminator sequence (Christie et al., (1981) Proc. Natl. Acad. Sci. USA 78:4180–4184) downstream of the gene. The same step could be carried out using Y1089 (Promega) or chromosomal DNA from any E. coli strain carrying the lac region, such as MM294 (ATCC 33625.) The PCR product was gel purified and isolated according to the Geneclean procedure and cloned into Bam HI-Hind III digested pUC19 DNA to make pSGE490.

Construction of pSGE515. PCR primers EV29 and EV18 were chosen to amplify the alpha gene from pDLII-91F (Hoffman et al., WO 90/13645). The purified PCR product was cleaved with the restriction endonucleases Eag I and Xba I.

To create a plasmid that contained $P_{tac}$-α, the alpha gene (from above) and the tac promoter, which was prepared by annealing EV27 and EV28, were mixed with Eco RI-Xba I cleaved pUC19 DNA. The mixture of the three DNA fragments, in approximately equimolar ratio, was treated with T4 DNA Ligase. After incubation the ligation mixture was used to transform SGE476 and ampicillin resistant transformants were selected. (Transformation into Strain MM294 (ATCC 33625) yields equivalent results.) An isolate with the correct restriction endonuclease fragments was designated pSGE492. The α gene and the tac promoter DNA sequences were verified by DNA sequencing.

Primers EV30 and EV31 were used to amplify the β gene from pSGE1.1IE4 by PCR. The purified β gene fragment was digested with Xba I and Hind III and then mixed with Xba I -Hind III digested pUC19 DNA and treated with T4 DNA ligase. The ligation mixture was used to transform competent SGE476 (equivalent to MM294, ATCC 33625) and transformants were selected on LB + ampicillin (100 μg/ml) plates. An isolate that contained the appropriate restriction endonuclease fragments (consistent with FIG. 1) was chosen and designated pSGE493. The β gene was confirmed by DNA sequencing.

The β gene was isolated from pSGE493 by restriction with Xba I and HindIII followed by purification according to the Geneclean method. This DNA fragment was then ligated to Xba I-Hind III restricted pSGE492 DNA and transformed into SGE713. (Any dam strain such as JM110 (ATCC 47013) or GM119 (ATCC 53339) could also be used.) An ampicillin resistant transformant that carried a plasmid that had the appropriate restriction fragments (consistent with FIG. 1) was chosen and designated pUC19αβ (pSGE500).

The Bam HI-Hind III fragment that contained the α and β genes of pSGE500 was purified according to the Geneclean method. An Xho I fragment that carried a portion of the di-α gene containing the glycine linker region was gel purified from pSGE1.1E5. pSGE1.E5 (described in Hoffman et al., U.S. Ser. No. 789,179, filed Nov. 8, 1991) is a tetracycline sensitive analogue of pSGE1.1E4 (Hoffman et al., WO 90/13645), which could also have been used.

The pBR322 origin of replication region (pBR322 ori, above) was ligated to the tet gene fragment (above) and the ligation mixture was transformed into SGE476. (Transformation into MM294, above would yield equivalent results.) Tetracycline resistant transformants were selected and plasmid DNA was isolated and analyzed. An isolate that contained the appropriate restriction endonuclease fragments (consistent with FIG. 1) was chosen and designated pSGE507.

Next, pSGE507 and pSGE490 were digested with Bam HI and Not I and the appropriate fragments were purified. The two purified fragments were ligated together and the ligation mixture was used to transform competent SGE713. Tetracycline resistant transformants were selected, and plasmid DNA was isolated and analyzed. A plasmid that had the appropriate restriction fragments was chosen and designated pSGE509.

The purified Bam HI-Hind III fragment of pSGE500 that contained the α and β genes was ligated to Bam HI-Hind III digested pSGE509. The ligation mixture was used to transform pSGE713 (see above for equivalent strains) and tetracycline resistant transformants were selected and characterized. An isolate yielding the correct size plasmid with the expected restriction endonuclease fragments was chosen and designated pSGE513.

The Xho I fragment of pSGE1.1E5 (described in Hoffman et al., U.S. Ser. No. 789,179, filed Nov. 8, 1991) that contained the di-α glycine linker sequence was ligated to Xho I digested pSGE513 to create a plasmid that contained the di-α gene. SGE753 was transformed with the ligation mixture and tetracycline resistant transformants were selected. (Transformation into SGE800 would have yielded equivalent results.) Isolates were screened to identify those that contained the Xho I fragment inserted into pSGE513 in the correct orientation (consistent with FIG. 1). An isolate that contained the correct configuration of the di-α gene, as determined by restriction endonuclease analysis with Eag I, was designated pSGE515.

Modification of pSGE515 to create pSGE705

The DNA sequence record used to design PCR primers for the amplification of the β gene did not contain the C-terminal three amino acids. Oligonucleotide directed mutagenesis was used to add these nine nucleotides to the DNA sequence of the β gene. In the same reactions, modifications were introduced to optimize the ribosome binding sites for the di-α and β genes, and to remove a Bgl II site near the end of the di-α gene.

The following are the changes that were made with the oligonucleotides MW008 and MW009 to optimize ribosomal binding sites and to remove a BglI restriction endonuclease site.

to optimize the ribosome binding site for beta. The lower case "a" on the before strand was a T to A mutation in the construction of the alpha gene that introduced a Bgl II site into the sequence. This was removed so that there would only be a single Bgl II site in pSGE705. (|)- indicates identity, *- indicates a change)

End of Beta

```
before  -  CTCGCTCAC---------TAATGAA    SEQ. ID #22
           |||||||||*********|||||||
after   -  CTCGCTCACAAATACCACTAATGAA    SEQ. ID #23
```

MW007 introduced the coding sequence for the last three amino acids of the beta gene as shown above. (|- indicates identity, *- indicates a change)

Putative mutants were screened for loss of a Bgl II restriction endonu- clease cleavage site (introduced by MW008). Seventeen of 24 had lost the site and were further characterized by DNA sequencing at the other two mutagenized sites. One of the 17 had incorporated all three modifications. These changes were verified by DNA sequencing and the rHb1.1 genes were cloned into Bam HI-Hind III digested pSGE509. An isolate that had the correct restriction endonudease fragments was designated pSGE705.

Figure 1B:
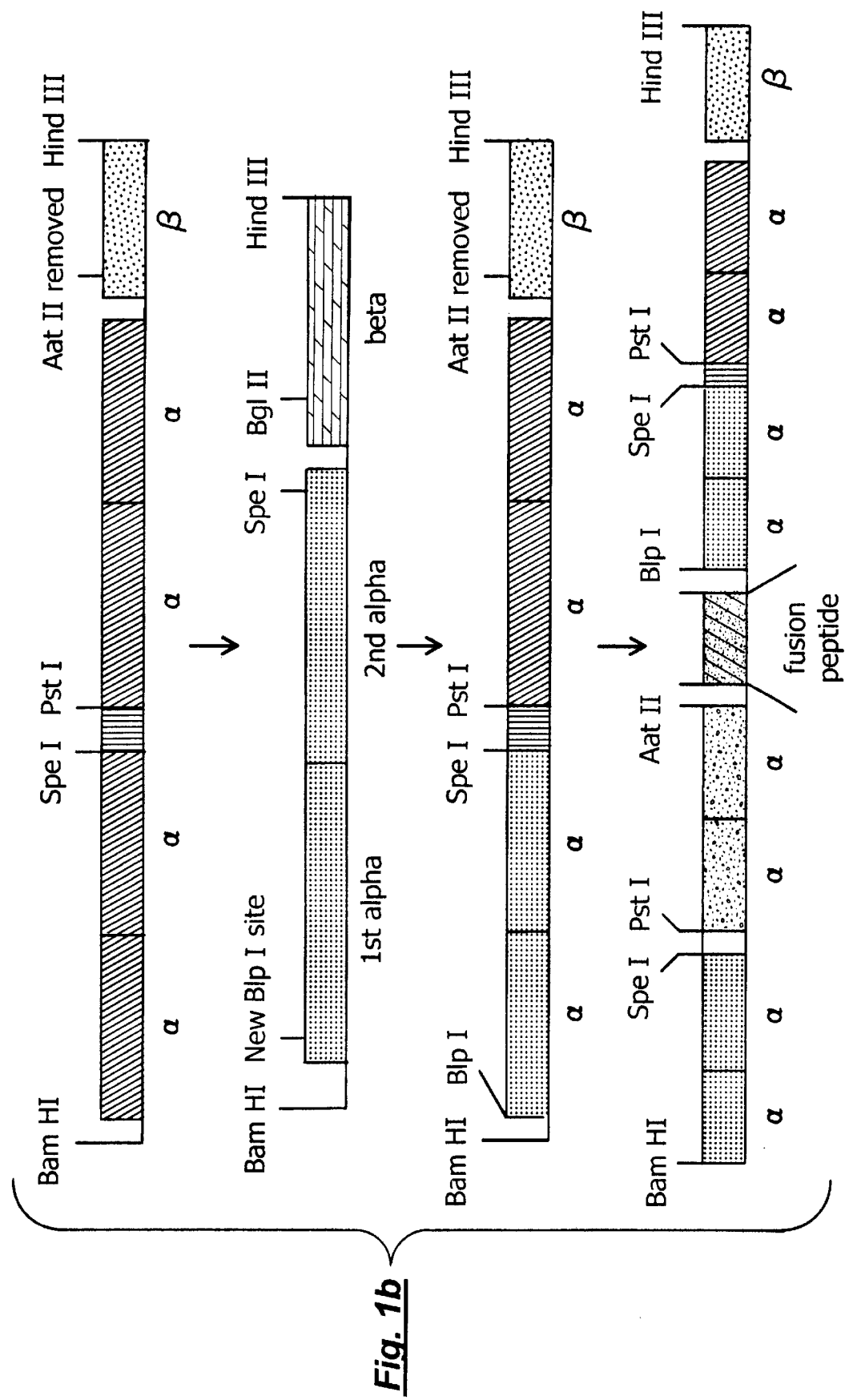

A plasmid map of pSGE705 is shown in FIG. 1. The plasmid map indicates many of the restriction endonuclease cleavage sites. pSGE705 is smaller than its counterpart pSGE1.1E4, and the placement of its restriction sites facilitates modular alterations of the sequence. An unused antibiotic resistance marker was removed, and a promoter was added to the lacI gene that would allow tighter control of rHb1.1 expression.

A new sequence upstream of the a gene minimized the distance between the tac promoter (De Boer et al., (1983) Proc. Natl. Acad. Sci. USA 80:21–25) and the first codon of the alpha gene. The intergenic region between the di-α gene and the β gene was also designed to contain the minimum sequence that contained a restriction endonuclease site and the ribosome binding site for the β gene.

On Jan. 20, 1994 E. coli strain SGE1661 was deposited with the American Type Culture Collection (ATCC Accession Number 55545) under the terms of the Budapest Treaty on the International Recognition of the Deposit of Microorganisms for the Purposes of Patent Procedure and the Regulations thereunder (Budapest Treaty). This assures di alpha

```
before  -  CAATTTCAC--AGGAAATTAATTAATGCTG    SEQ. ID #18
           |||||||||**||||**|||||||||||||
after   -  CAATTTCACTAAGGAGGTTAATTAATGCTG    SEQ. ID #19
```

Four nucleotide changes, shown above, including the insertion of two nucleotides, were introduced with MW008 to optimize the ribosome binding site for di-alpha. (|- indicates identity, *- indicates a change)

maintenance of a viable culture for 30 years from the date of deposit. The organisms will be made available by the ATCC under the terms of the Budapest Treaty, and subject to an agreement between Applicants and ATCC which assures beta

```
before  -  TAAaGATCTAGA---GGAAATAA-TATATGCAC    SEQ. ID #20
           |||*|||||||||***|||**|||*|||||||||
after   -  TAATGATCTAGATAAGGAGGTAAATATATGCAC    SEQ. ID #21
```

The six nucleotide changes shown above, including the insertion of four nucleotides, were introduced with MW009 unrestricted availability upon issuance of the pertinent U.S. patent. Availability of deposited strains is not to be construed as a license to practice the invention in contravention of the rights granted under the authority of any government in accordance with its patent laws.

B. Fermentations

Fermentor Inoculum (500 mL broth in 2 L shake flasks)

To prepare the fermentor inoculum, seed stock was thawed. Seed stock (100 μl) was grown up in 500 ml of DM1 in an Erlenmeyer flask at 37° C. in a 1 inch rotary shaker (275 to 300 rpm) for 8 to 10 hours. DM1 media is:

4.1 g/L $KH_2PO_4$
7.0 g/L $K_2HPO_4$
2.0 g/L $(NH_4)_2SO_4$
1.0 g/L $Na_3Citrate. 2H_2O$
153 mg/L $MgSO_4$, .$7H_2O$
up to 2.30 g/L of L-proline, 2.5 mL/L of a trace metal solution containing:
  32.5 μ/ml $FeCl_3.6H_2O$
  1.56 μ/ml $ZnCl_2$
  2.4 μ/ml $CoCl_2.6H_2O$, 2.4 μ/ml $Na_2MoO_4.2H_2O$,
  1.22 mg/mL $CaCl_2.2H_2O$,
  1.54 μg/ml $Cu(II)SO_4.5H_2O$,
  0.6 μg/ml $H_3BO_3$,
  120 μl/ml HCl dissolved in purified water After sterilization of the above solution, the following components were added to achieve the final concentrations indicated:

20 mL/L 10% yeast extract/L
4.0 mL 60% glucose solution/L
0.06 mg/L of sterile-filtered 125 mg/mL thiamine HCl dissolved in purified water
0.1 mg/L of tetracydine in an ~ 50% ethanol solution Fermentor (2 L volume)

200 mL of the Fermentor Inoculum was then asceptically transferred to a 2-liter New Brunswick fermentor containing 1800 mL of a solution containing:

1.83 g/ L $KH_2PO_4$
3.27g/L $K_2HPO_4$
1.83 g/L $(NH_4)_2SO_4$

After sterilization of the above solution, the following components were added to achieve the final concentrations indicated:

1.36 g/L TriSodium Citrate
1.36 g/L $MgSO_4.7H_2O$
2.87g/L proline
3.05 g/L of the Trace Metal solution described above
0.1 mg/L tetracycline in 50% ethanol solution,
0.06 mg/L thiamine HCl in purified water, sterile filtered solution
200 g/L of 70% glucose
50+10 g/L of30% $NH_4OH$
2 ml PPG 2000

The fermentor is run at 30±1° C., controlling dissolved oxygen at 20% and glucose between 0–6 g/L. At OD 30± 2, induction occurs by adding 1.4 mL of 100 mM Isopropyl thiogalactoside (IPTG) and 1.5 mL of 50 mg/mL hemin. At 3 hours post induction, 2.0 mL of 50 mg/mL hemin is added and at 6 hours post induction, 2.5 mL of 50 mg/mL hemin is added. Harvest and further purification occurs at 10 hours post induction.

C. Purification

Frozen cells were partially thawed in warm water for approximately 20–30 minutes. Cells were chopped into small bits in a steel beaker using break buffer (40 mM Tris base, 1 mM benzamidine) as needed. The chopped cells and break buffer at a ratio of 2 mL break buffer per 1 gram of frozen cells were placed in a Waring Industrial Blender and homogenized for 3–5 minutes on the low setting. The solution was allowed to settle for 5 minutes after homogenization and any foamed material was removed.

A Niro Panda™ cell disruption device (Niro Hudson, Inc. Hudson, Wis.) was used for homogenization by passing 200 mL of buffer through the system. Cells were lysed by two passages of the homogenized cell solution through the Niro set at 850 bar. The pH of the lysate was adjusted to approximately 8 with sodium hydroxide, and sufficient $Zn(OAc)_2$ was added to make the solution 2 mM in $Zn(OAC)_2$. The solution was then spun at 10,000 rpm in a JA-10 rotor at 4° C. for 60 minutes in a Beckman centrifuge. The supernatant was collected and diluted 1:1 with distilled water.

Chromatography

All solutions were 4° C. and were adjusted to the correct pH at 4° C. 500 mL of Chelating Sepharose fast flow resin (Pharmacia, Piscataway, N.J.) was prepared by washing with 4 column volumes of distilled water. Flow through the column for all steps was 200 mL/min. The resin was charged with 2 to 3 column volumes of 2mM $Zn(OAc)_2$ followed by 2–3 column volumes of 200 mM NaCl. The lysate was loaded onto the column and washed with 4 to 6 column volumes of 20 mM Tris, 500 mM NaCl, pH 8.5, 7–8 column volumes of 240 mM Tris, pH 8.5, and 7–8 column volumes of 20 mM Tris, pH 8.5. Hemoglobin was eluted with 15 mM EDTA, 20 mM Tris, pH 8.5 and collected into 200 mL of well oxygenated 20 mM Tris, pH 8.5. The column was then rinsed with an additional 3–4 column volumes of 15 mM EDTA, 20 mM Tris, pH 8.5, regenerated with 4 column volumes of 200 mM NaCl and stored in 0.2 N NaOH.

The solution was then buffer exchange 5 times into 20 mM Tris, pH 8.5 prior to loading onto 200 mL of a Sepharose Q column. The column had been prepared by rinsing with 4 column volumes of distilled water, 4 column volumes of 1 M NaCl, 4 additional column volumes of distilled water and equilibrating with 3 to 4 column volumes of 20 mM Tris, pH 8.5. After loading the sample, the column was washed with 2 to 3 column volumes of 20 mM Tris, pH 8.5 and eluted with 20 mM Tris, pH 7.6. Fractions were collected and pooled if the $A_{575}/A_{540}$ ratio was greater than or equal to 1.03. The column was then cleaned with 3–4 column volumes of 1 M NaCl, 4 column volumes of distilled water, 2–3 column volumes of 50% acetic acid, 4 column volumes of distilled water and finally 2–3 column volumes of 0.2 N NaOH for storage. The column was run at 30 mL/min flow rate. The resultant hemoglobin was stored at −80° C. or in liquid nitrogen.

EXAMPLE 2

Construction of di di-alpha Gene Construct

A. Construction of pTZ19U/705 Mutants

The rHb1.1 genes were cloned as a BamHI/HindIII DNA fragment into pTZ19U (BioRad, Hercules, Calif.) in the MCS Region as described in the cloning procedure of Example 1. This construct was then transformed using a modified process of the Hanahan protocol (Hanahan, *J. Mol. Biol.*, 166:557 1983) into CJ236 *E. coli* strain (BioRad). The modified process is described in Example 7. Single-stranded DNA containing uracil substitutions was isolated and oligonucleotide-directed mutagenesis was performed using the Muta-gene Kit (BioRad) and standard protocols according to the manufacturer's instructions. Two pTZ19U/705 clones were prepared using oligonucleotides.

The first pTZ19U/705 clone was prepared using oligonucleotide JD29, which has the sequence: ACC GTT CTG ACT AGT AAA TAC CGT TAA TGA (SEQ.ID.NO.24). This oligonucleotide created a unique SpeI site in the end of the di-alpha domains.

The second pTZ19U/705 clone was prepared using the two oligonucleotides JD28 and JD30. JD28 has the sequence: 5'-GGA GGT TAA TTA ATG CTG TCT CCT GCA GAT-3'(SEQ.ID.NO.25). JD30 has the sequence: 5'-CTG GTG GGT AAA GTT CTG GTT TGC GTT CTG-3' (SEQ.ID.NO.26). The resulting clone incorporated a unique PstI site in the di-alpha genes and removed an SpeI site in the beta domain.

B. Assembly of the di di-alpha gene construct

The assembly of di di-alpha gene construct was accomplished by removing a di-alpha gene cassette from the first pTZ19U/705 clone using BamHI/SpeI enzymes and gel purifying the DNA fragment. The second pTZ19U/705 clone was cut with SpeI/BglII enzymes to give a second di-alpha gene cassette with the 5' end of the beta gene, which was also purified. These were then ligated together with annealed oligos JA113 and JA114 to create a di di-alpha cassette with a 7 amino acid fusion peptide linker.

JA113: 5'- CT AGT AAA TAC CGA TCG GGT GGC TCT GGC GGT TCT GTT CTG TCT CCT GCA-3' (SEQ. ID. NO. 27).

JA114: 5'- GG AGA CAG AAC AGA ACC GCC AGA GCC ACC CGA TCG GTA TTT A-3' (SEQ. ID. NO. 28).

This di di-alpha cassette was then ligated as a BamHI/BglII fragment into pSGE705 that had the rHb1.1 genes removed as a BamHI/BglII fragment. The resulting di di-alpha plasmid (pSGE1000) was transformed into SGE1661 using Hanihan's protocol to create SGE939.

EXAMPLE 3

Construction of a High Copy Plasmid

The construction of pSGE720 was performed in two stages. First, the pUC origin of replication was introduced to create plasmid pSGE715, which is similar to pSGE705 in that it includes the lacI gene. Then, the lacI gene was deleted from the plasmid and replaced with a short oligonucleotide containing several convenient restriction sites to create plasmid pSGE720.

A. Construction of pSGE715

The pUC origin of replication was introduced to create plasmid pSGE715 through pSGE508, which is identical to pSGE509 with the exception of a single basepair substitution at base 602 (G→A). The substitution changes the pBR322 origin of replication to a pUC19 origin of replication.

Plasmids pSGE508 and pSGE705 were digested to completion with restriction enzymes BamHI and HindIII, according to the manufacturer's instructions (New England Biolabs.). The plasmid, pSGE508, was digested first with BamHI to completion, then HindIII was added, and the digestion continued. The pSGE705 digest was purified with Promega Magic DNA Clean-up protocols and reagents (Promega, Madison, Wis.) and further digested to completion with BglI, according to the manufacturer's instructions (New England Biolabs). The enzymes in both pSGE508 and pSGE705 digests were inactivated by heating at 67° C. for 10 minutes, then the DNA was pooled and purified together using Promega Magic DNA Clean-up protocols and reagents. The DNA was suspended in ligation buffer, T4 DNA ligase was added to one aliquot, and the DNA was incubated overnight at 16° C. SGE1661 cells were made competent by the method of Hanahan, using Rubidium Chloride (Hanahan, D., 1985. In *DNA Cloning; A Practical Approach* (Glover, D. M., ed.) vol. 1, pp.109–135, IRL Press, Oxford), and transformed with the ligation mix according to the Hanahan protocol. Transformants were selected by plating the cells on LB plates containing 15 g/ml tetracycline. Candidates were screened by restriction digestion to determine the presence of the rHb1.1 genes, and sequencing to detect the pUC origin of replication. Several candidates were identified, and the resulting plasmid was named pSGE715, and pSGE715 in SGE1661 was called SGE1453.

The copy number of pSGE715 is about four-fold higher than pSGE705, measured to be about 460 plasmids per cell. As noted above, the difference between pSGE705 and pSGE715 is a single basepair change in the origin of replication region, which has been confirmed by sequencing.

B. Construction of pSGE720

The lacI gene was deleted from pSGE715, replacing it with a short oligonucleotide containing several convenient restriction sites, by the following steps. First, plasmid pSGE715 was digested to completion with restriction enzymes BamHI and NotI, according to the manufacturer's instructions (New England Biolabs). The pSGE715 digest was purified with Promega Magic DNA Clean-up protocols and reagents. The DNA was mixed with annealed, kinased oligonucleotides, CBG17+CBG18, and suspended in ligation buffer.

CBG17 = 5'-GGCCGCCTTAAGTACCCGGGTTTCTGCAGAAAGCCCGCCTA ATGAGCGGGCTTTTTTTTCCTTAGGG-3' (SEQ. ID. No. 29)

CBG18 = 5'-GATCCCCTAAGGAAAAAAAAGCCCGCTCATTAGGCGGGCTTT CTGCAGAAACCCGGGTACTTAAGGC-3') (SEQ. ID. NO. 30)

T4 DNA ligase was added to one aliquot, and the DNA was incubated overnight at 16° C. SGE1821 cells were made competent by the method of Hanahan, using Rubidium Chloride, and transformed with the ligation mix according to the Hanahan protocol. Transformants were selected by plating the cells on LB plates containing 15 g/ml tetracycline. Candidates were screened by restriction digestion using PstI and SmaI to detect the presence of the new linker and the absence of the lacI gene, and sequenced to detect the pUC origin of replication and the absence of the lacI gene. Several candidates were identified, and the resulting plasmid was named pSGE720. The plasmid, pSGE720, in SGE1675 is called SGE1464.

EXAMPLE 4

High copy Di di-alpha Construct

A second plasmid containing the di di-alpha hemoglobin genes was created using pSGE720 as the vector. The di di-alpha gene cassette was removed as a BamHI/HindIII fragment and gel purified. The vector pSGE720 was also cut with BamHI/HindIII and the rHb1.1 genes removed. The vector was gel purified. The di di-alpha cassette was ligated into the pSGE720 vector, resulting in a new vector pSGE1004. This new vector was then transformed into *E. coli* strain SGE1675 using the modified Hanahan method as described below to produce strain SGE946.

EXAMPLE 5

Characterization of SGE939 and SGE946 Hb Globins

Several 15 liter fermentations were performed on both strains SGE939 and SGE946 and soluble vs. insoluble western blots were performed using conventional methods. This data coupled with purification yields indicated that more soluble protein could be obtained from SGE946 (250–300 mg/L by the BioCAD assay (BioRad). The data obtained shows that both strains make di di-alpha globin and beta globin proteins, but that the SGE946 strain makes a larger amount of total protein and soluble protein.

The SGE939 hemoglobin-like protein was first eluted from a Q-sepharose column and then from a S-sepharose column on an FPLC. Fractions were collected by eluting with a pH gradient. By SDSPAGE analysis, there appears to be a population of degradation products since these cross-react with anti-rHb antibodies. The cleanest fractions were pooled and analyzed by C4 HPLC. A chromatogram of SGE939 showed the beta globin eluting at 43.7 minutes as expected, and the di di-alpha peak eluting at 61.8 minutes. Di-alpha globin normally elutes at about 55 minutes under these conditions. There is also a peak at 56.2 minutes and a large shoulder on the di di-alpha peak. The peaks were collected and analyzed by mass spectroscopy. The beta globin peak gave the expected molecular weight of 15,910 daltons, while the di di-alpha peak gave a molecular weight of 61,108 daltons. The calculated molecular weight for di di-alpha globin is 61,107.8 daltons. These results indicate that the protein expressed from SGE939 contains the expected di di-alpha polypeptide. The protoporphyrin IX content was shown to be below 3%. The $P_{50}$ averaged to be 24.7 and the $n_{max}$ was 1.75. These values fall within the acceptable range for a functional oxygen delivery vehicle.

EXAMPLE 6

TETRA DI-ALPHA

A. Construction of di-dialpha vector containing K158C mutation

Replacing the lysine residue at position 158 of di-alpha globin allows chemical cross-linking of rHb1.1 molecules to form a dimeric hemoglobin molecule referred to as K158C. This mutation can be inserted into the di-dialpha expression plasmid (pSGE1000), to produce a mutant genetically linked di-hemoglobin that can be chemically cross-linked to form a tetra-hemoglobin. The modification will place the K158C mutation in the fourth (3'-terminal) alpha globin coding sequence of the di-dialpha plasmid. The K158C mutation is a 3 base change in the coding sequence, and can be transferred among dialpha containing vectors on an Eag I-Bgl II restriction fragment. Because there are multiple Eag I sites in pSGE1000, an intermediate cloning step in the plasmid "pFusion II" is required. The cloning steps are as follows:

1. Isolate an EagI - Bgl II fragment containing the K158C mutation from plasmid 1.1E4
2. Isolate large Eag I - Bgl II fragment from plasmid pFusion II, which removes the comparable "wild type" fragment from the second alpha gene
3. Ligate above fragments to form the intermediate pFusion II—based vector containing the K158C mutation
4. Replace the Pst I-Bgl II fragment in pSGE1000 with the Pst I-Bgl II fragment containing the K158C mutation.

B. Development of a cloning strategy for genetically linked tetra di-alpha

Expression of a genetically linked tetra-hemoglobin molecule requires construction of a plasmid containing coding sequences for four dialpha hemoglobin genes, connected by coding sequences for peptide linkers, and one beta globin gene. A plasmid with these characteristics can be based on pSGE1000, which is currently being used to express a genetically linked di-hemoglobin. The following steps will be required to generate this plasmid:

1. Generate a modified vector with a new restriction site at the 5'end of the di-dialpha coding sequence;
2. Generate a second modified vector with a new restriction site at the 3' end of the di-dialpha coding sequence;
3. Design an amino acid sequence suitable for linking the di-dialpha molecules in such a way that a tetra-hemoglobin can assemble and design the DNA sequence required to encode the peptide linker; and
4. Assemble a new plasmid containing the two modified di-dialpha sequences, the linker sequence, and either a 705 or 720 plasmid background.

The coding sequence of pSGE1000 has been entered into the computer in the DNA Strider program, and confirmed. The PINCERS program was utilized to locate silent mutations in the di-dialpha sequence that will generate restriction sites unique to di-dialpha in either the 705 or 720 (low and high-copy) plasmid backgrounds, near the 5' and 3' ends of the di-dialpha coding sequence. Two possible restriction sites have been identified, pending digestion of the appropriate plasmids to ensure the uniqueness of the sites. A restriction site for one of the enzymes, AatII, is also present in the beta globin gene; this will necessitate removal of this recognition sequence by site-directed mutagenesis, introducing an additional step in the construction of the tetra-hemoglobin expression vector. A preliminary cloning strategy has been generated for construction of a tetra-hemoglobin expression vector. A schematic for the cloning steps is provided in FIG. 1 and the following:

1. The target is a BamHI/HindII fragment containing a tetra-hemoglobin coding sequence as shown in FIG. 1 (first).
2. Create an Aat II site at the 3' end of the dialpha gene in pFusion II by site directed mutagenesis as shown in FIG. 1 (second).
3. Subclone mutant into di dialpha on a PstI/Bg1II restriction fragment as shown in FIG. 1 (third).
4. Remove AatII site from beta globin gene in pFusion II by site directed mutagenesis as shown in FIG. 1 (fourth).
5. Subclone mutant into a second di di-alpha construction o a PstI/Bg1II fragment as shown in FIG. 1 (fifth).
6. Create a BlpI site at the 5' end of the dialpha gene in pFusion I by site directed mutagenesis (sixth) of FIG. 1.

7. Subclone mutant on a BamHI/Spe I fragment into the modified di dialpha plasmid of step 5 (seventh) of FIG. 1.
8. Isolate BamHI/AatII fragment from step 3, and the B1pI/HindII fragment from step 7; ligate with a new synthetic sequence encoding a peptide linker, and with the 705 plasmid background.

EXAMPLE 7

General Transformation Procedure

A modified Hanahan protocol was used to produce competent *E. Coli* cells. The Hanahan Transformation buffer contains 45 mM $MnCl_2$, 60 mM $CaCl_2$, 40 mM KoAc, 620 mM sucrose, 15% glycerol and 100 mM Rubidium chloride. A 5 ml culture of an *E.coli* strain was started in 2× TY broth from an isolated colony and cultured overnight. Then, 200 ml of 2× TY broth was innoculated with 2 ml of the overnight culture and incubated at 37° C. with vigorous shaking for 2.5 hours. The culture was then transferred to two 300 ml centrifuge tubes and placed on ice for 15 minutes. Cells were pelleted in a centrifuge at 8K rpm's, 4° C., for 10 minutes and the supernatant was poured off. Gently, but thoroughly the cells were resuspended cells in 80 ml transformation buffer. The cells were again pelleted at 8K, 10 minutes and 4° C. The cells were gently resuspended in 20 ml of ice-cold transformation buffer and left on ice for 30–60 minutes. Cells were aliquoted in buffer into twenty 1 ml tubes. The cells were quickly frozen on dry ice and stored at −80° C.

EXAMPLE 8

Preparation of BMH-crosslinked di-K158C

Bismaleimidohexane (BMH) was purchased from Pierce Chemical Co. (Rockford, Ill.). BMH is a homobifunctional maleimide crosslinker, and its primary reactivity is towards sulfhydryl residues. The linkage is irreversible once formed. The alkane spacer between the maleimide residues is hexane (six carbons) and the molecule has poor solubility in buffered aqueous solutions. The nominal length of the crosslinker is 16.1Å.

The rHb is concentrated to 60 mg/mL in 20 mM Tris buffer pH 8, and converted into the deoxygenated state by gas exchange in a rotating glass flask through which humid oxygen free nitrogen is passed. The ligation state of the rhb1.1[K158C] is controlled as the deoxy form to limit reaction of the BMH with the intrinsic sulfhydryls of hemoglobin, especially residue Cys93. The reactivity of this residue with sulfhydryl reactive reagents is generally at least 50 fold slower in the deoxy form than in liganded forms of hemoglobin. The reactivity of the surface K158C residue is not affected significantly by the heme ligation state.

A solution of BMH is prepared in pure dimethyl sulfoxide (DMSO) at 10 mg/mL. An aliquot of this solution is added to the deoxyHb solution (0.6 moles of BMH per mole of Hb, maintaining deoxy conditions) with swirling to mix, and the sample is allowed to react for 1 hour on ice. Following reaction the Hb solution is centrifuged or filtered (0.2 micron) to remove any precipitated material, diluted to 25 mg/mL and then chromatographed on Sephacryl S-200 HR to resolve the diHb fraction from the unreacted monoHb and the small amount of triHb formed during the reaction. Two S-200 HR columins (Pharmacia BPP 113, ca. 5L of resin each, 11.3 cm diameter×60 cm) are used in series to give acceptable resolution and volume handling capabilities. The yield of coupling is typically 60%, and about 50% of the starting Hb is recovered following size exclusion chromatography. Following chromatography on Q-sepharose to remove endotoxin, the diHb was submitted for several routine analyses and the results are reported below.

| Assay | Result |
|---|---|
| Endotoxin (LAL assay) | 0.6 EU/mL |
| ECP | BLD |
| PPIX | 1.14% |
| p50, Torr at 37° C. | 32.7 |
| Nmax. | 2.09 |
| % Oxygen delivered | 29.5 |

Example 10

LAL Assay for Endotoxin

Fifty microliters of endotoxin standard, blank diluent, or hemoglobin solution (rHb1.1, Somatogen, Inc., Boulder, Colo.) was mixed with 50 µl of LAL lysate (BioWhittaker, Inc., Walkersville, Md.) in a well of a 96-well, pyrogen-free microtiter plate, according to the manufacturer's instructions. The mixture was allowed to incubate for 30 minutes in a 37° C. water bath. One hundred microliters of the chromogenic substrate was added to each well and the plate allowed to incubate for an additional 16 to 60 minutes at 37° C. The reaction was stopped by the addition of 50 µl 25% glacial acetic acid, and the samples transferred to HPLC sample vials for analysis.

Twenty microliters of each sample was injected onto a Vydac C4-reversed phase chromatography column (2 mm×250 mm), pre-equilibrated at 40° C., 5% Solvent B. (Solvent A is 20% acetonitrile in water with 0.1% TFA and Solvent B is 100% acetonitrile with 0.1% TFA). Conditions for separation were as follows: flow was about 1 ml/min, with 5% Solvent B and 95% Solvent A, hold at 5% Solvent B and 95% Solvent A for 1 min, increased to 50% Solvent B over 4 minutes, then increased to 100% Solvent B over a 2 minute period, washed at 100% Solvent B for 3 minutes, returned to 5% Solvent B and 95% Solvent A over a 1 minute period and equilibrated at 5% Solvent B and 95% Solvent A for 4 minutes. The separation was monitored at 405 nm.

The peak areas of the standard solutions were used to construct a standard curve against which test samples were measured. A series of curves can be generated from the analysis of standard solutions ranging in concentrations from 0.5 EU/ml to 0.0005 EU/ml. Linearity is achieved when the standards are analyzed in groups according to the time of incubation. One curve can be generated from analysis of samples incubated with chromogenic substrate for 16 minutes, curves 2 and 3 can be generated from analysis of samples incubated with chromogenic substrate for 30 minutes, while curve 4 can be generated from analysis of samples incubated with chromogenic substrate for a total of 60 minutes. Therefore, a standard curve for use in a particular circumstance will depend on the endotoxin concentration range being measured and the appropriate length of incubation. The sensitivity of this assay can also be regulated by changing the incubation times.

EXAMPLE 11

Construction of rHb1.1/K158C Multimeric Proteins
5 A. Preparation of rHb.1.1/(K158)$_4$ Multimer
Sulfosuccinimidyl 4-(N-maleimidomethyl)cyclohexane-1-carboxylate (Sulfo-SMCC) was purchased from Pierce Chemicals (Rockford, Ill.). Sulfo-SMCC is a water soluble heterobifunctional crosslinker that reacts with both amine and sulfhydryl functional groups. Reaction with lysine residues on rHb1.1 leads to loss of the sulfosuccinimide group with the formation of a stable amide linkage between the protein and the N-(4-carboxy-cyclohexylmethylmaleimide) moiety. These residues are highly reactive towards sulfhydryl groups and following reaction with sulfo-SMCC, the rHb1.1 has been "activated" at multiple surface lysine residues towards reaction with the surface sulfhydryl residue of K158C. The N-(4-carboxy-cyclohexylmethylmaleimide) residues are particularly stable to hydrolysis and the "activated" rHb1.1 can thus be manipulated extensively prior to addition of K158C. The desired extent of modification of rHb1.1 was determined empirically by reaction with K158C following activation. The initial reaction with sulfo-SMCC was modulated by altering the concentration of sulfo-SMCC and reaction time, until a covalent Hb polymer of the desired size range was achieved upon subsequent reaction with K158C. Once determined, these conditions were used throughout. In determining these conditions, the stability of the polymer was monitored. If the extent of reaction with sulfo-SMCC is too great the resulting polymer is unstable towards freeze-thawing and precipitates.

A solution of sulfo-SMCC, 10 mg/mL in 100 mM sodium borate buffer pH 8.5, was added to a solution of rHb1.1 (30 mg/mL) to a 35 molar excess over moles of Hb. The mixture was allowed to react at 20° C. for 30 minutes after which the remaining unreacted crosslinker was quenched by the addition of a 100 fold excess of Tris buffer pH 8.5.

The reaction mixture was then chromatographed on Sephadex G-25 to remove quenched crosslinker, borate ions, and to buffer exchange the activated rHb1.1 into 50 mM Tris-Cl buffer, pH 8.0. Following buffer exchange the activated rHb1.1 was concentrated to 15 mg/mL and converted into the deoxy form as described for the preparation of BMH crosslinked diHb. An aliquot of deoxygenated K158C (60 mg/ml in same buffer) was added to the activated deoxyrHb1.1 to final ratio of 6 K158C:1 rHb1.1. This mixture was allowed to react at 4° C. for 16 hours. After this time the desired molecular weight fraction was resolved from the mixture by size exclusion chromatography on Sephacryl S-200 HR and S-300 HR. Two columns (Pharmacia BPP113, 60 cm length, one of each resin type) were used in series to achieve the desired fractionation. Both columns were equilibrated with phosphate buffered saline, pH 7.5.

Alternately, size fractionation can be achieved by ion exchange chromatography on Q-Sepharose FF resin. The undesired triHb, diHb, and monoHb fractions are retained on the resin because they have chromatographic interaction sites which are accessible to the resin. The desired polymer does not bind to the Q-Sepharose and simply flows through, and thus efficient size fractionation is achieved.

The pentaHb fraction exhibited the following equilibrium oxygen binding properties: $P_{50}$=31.9, 27.4 Torr and $N_{max}$= 1.73, 1.72 respectively, for two preparations.

B. Preparation of K158C Homomultimer

An entire multimeric Hb-like protein can be prepared using only K158C tetramers. The use of borate buffer protects the K158C sulfhiydryl residues in the first step during which lysine residues on the hemoglobin react with the amine reactive half of the heterobifunctional crosslinker. Thus, in the presence of borate buffer, only the amine reactive function of the crosslinker reacts and K158C is modified in the desired fashion. This leaves the unreacted surface sulfhydryl residue (Cys158) available for later reaction with the sulfhydryl reactive portion of the crosslinker. In subsequent steps, the quenched (excess) crosslinker is removed by gel filtration or tangential flow ultrafiltration in the continued presence of borate buffer. Borate buffer should be maintained while any sulfhydryl reactive crosslinker is being removed. Following adequate removal of the (amine) quenched crosslinker, the borate buffer is exchanged completely for a suitable deprotecting buffer, such as Tris-Cl buffer, (gel filtration or tangential low ultrafiltration). This deprotects the K158C surface sulfhydryl residue to enable the final crosslinking step in which pentaHb is produced. Borate/boric acid buffer seems to be very effective at blocking sulfhydryl reactivity at considerably less than 100 mM total borate species.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

---

What is claimed is:

1. A purified globin-like polypeptide comprising two di-alpha domains.

2. The globin-like polypeptide of claim 1, wherein the two di-alpha domains are coupled by a peptide linker.

3. The globin-like polypeptide of claim 2, wherein the peptide linker comprises an amino acid sequence of at least seven amino acids.

4. The globin-like polypeptide of claim 3, wherein the peptide linker comprises Ser-Gly-Gly.

5. The globin-like polypeptide of claim 4, wherein the amino acid sequence is SEQ.ID.No.1.

6. The globin-like polypeptide of claim 4, wherein the amino acid sequence is SEQ.ID.No.2.

7. The globin-like polypeptide of claim 4, wherein the amino acid sequence is SEQ.ID.No.3.

8. The globin-like polypeptide of claim 1, wherein the polypeptide is expressed by a recombinant host cell.

9. The globin-like polypeptide of claim 8, wherein the host cell is E. coli.

10. The globin-like polypeptide of claim 1, wherein said polypeptide contains a cysteine residue capable of attaching to an endogenous crosslinker.

11. The purified globin-like polypeptide of claim 1 consisting essentially of two di-alpha globins.

12. The purified globin-like polypeptide of claim 1, wherein said globin-like polypeptide is a recombinant polypeptide.

13. A multimeric hemoglobin-like protein comprising a core hemoglobin-like moiety to which each of at least two other hemoglobin-like moieties are directly attached to the core hemoglobin-like moiety.

14. The multimeric hemoglobin-like protein of claim 13, wherein the core hemoglobin-like moiety is directly attached to four other hemoglobin-like moieties.

15. The multimeric hemoglobin-like protein of claim 13, wherein the core hemoglobin-like moiety is different than the other hemoglobin-like moieties.

16. The multimeric hemoglobin-like protein of claim 13, wherein said other hemoglobin-like moieties contain an asymmetric crosslinkable cysteine residue for attachment to the core hemoglobin-like moiety.

17. The multimeric hemoglobin-like protein of claim 16, wherein the other hemoglobin-like moieties are attached to the core hemoglobin-like moiety by a chemical crosslinker.

18. The multimeric hemoglobin-like protein of claim 17, wherein the chemical crosslinker is a succinimidyl 4-(N-maleimidomethyl)cyclohexane-1-carboxylate.

19. The multimeric hemoglobin-like protein of claim 18, wherein the core hemoglobin-like moiety is rHb1.1 and the other hemoglobin-like moieties are K158C.

20. The multimeric hemoglobin-like protein of claim 13, wherein the core hemoglobin-like moiety is the same as the other hemoglobin-like moieties.

21. The multimeric hemoglobin-like protein of claim 20, wherein the core hemoglobin-like moiety is K158C.

22. A method for making a multimeric hemoglobin-like protein, comprising:

(a) obtaining a first hemoglobin-like moiety having an amino acid capable of attaching to one end of a heterobifunctional linker to form a core hemoglobin-like moiety;

(b) obtaining at least two other hemoglobin-like moieties having an amino acid capable of attaching to the other end of the heterobifunctional linker;

(c) contacting the heterobifunctional linker to the core hemoglobin-like moiety to form a linked moiety; and (d) contacting the other hemoglobin-like moieties to the linked moiety to form the multimeric hemoglobin-like protein.

23. A composition comprising a multimer hemoglobin-like protein having a core hemoglobin-like moiety to which each of at least two other hemoglobin-like moieties are directly attached to the core hemoglobin-like moiety.

* * * * *